United States Patent
Chudik

(10) Patent No.: US 9,974,658 B2
(45) Date of Patent: May 22, 2018

(54) GLENOID IMPLANT FOR MINIMALLY INVASIVE SHOULDER REPLACEMENT SURGERY

(76) Inventor: Steven C. Chudik, Western Springs, IL (US)

( * ) Notice: Subject to any disclaimer, the term of this patent is extended or adjusted under 35 U.S.C. 154(b) by 1489 days.

(21) Appl. No.: 11/525,631

(22) Filed: Sep. 25, 2006

(65) Prior Publication Data
US 2007/0016304 A1    Jan. 18, 2007

Related U.S. Application Data

(62) Division of application No. 10/917,266, filed on Aug. 11, 2004.

(60) Provisional application No. 60/494,289, filed on Aug. 11, 2003, provisional application No. 60/509,655, filed on Oct. 8, 2003, provisional application No. 60/511,805, filed on Oct. 16, 2003, provisional application No. 60/523,401, filed on Nov. 19, 2003, (Continued)

(51) Int. Cl.
| | |
|---|---|
| A61F 2/40 | (2006.01) |
| A61B 17/17 | (2006.01) |
| A61B 17/88 | (2006.01) |
| A61F 2/46 | (2006.01) |
| A61B 17/16 | (2006.01) |
| A61F 2/30 | (2006.01) |
| A61B 90/00 | (2016.01) |

(52) U.S. Cl.
CPC ........ *A61F 2/4003* (2013.01); *A61B 17/1684* (2013.01); *A61B 17/1703* (2013.01); *A61B 17/1721* (2013.01); *A61B 17/1778* (2016.11); *A61B 17/8875* (2013.01); *A61F 2/4612* (2013.01); *A61B 17/1604* (2013.01); *A61B 17/1606* (2013.01); *A61B 17/1617* (2013.01); *A61B 17/1637* (2013.01); *A61B 17/1735* (2013.01); *A61B 2090/061* (2016.02); *A61B 2090/08021* (2016.02); *A61F 2/30767* (2013.01); *A61F 2/4081* (2013.01); *A61F 2/4684* (2013.01); *A61F 2002/30604* (2013.01); *A61F 2002/30934* (2013.01); *A61F 2002/4018* (2013.01); *A61F 2002/4635* (2013.01); *A61F 2310/00017* (2013.01); *A61F 2310/00023* (2013.01); *A61F 2310/00131* (2013.01); *A61F 2310/00179* (2013.01)

(58) Field of Classification Search
USPC ......... 623/19.11, 19.12, 19.13, 22.21, 22.23, 623/22.24, 22.25, 22.33, 22.38, 23.11
See application file for complete search history.

(56) References Cited

U.S. PATENT DOCUMENTS

| | | | |
|---|---|---|---|
| 4,261,062 A * | 4/1981 | Amstutz et al. | 623/19.13 |
| 5,080,673 A * | 1/1992 | Burkhead et al. | 623/19.11 |

(Continued)

FOREIGN PATENT DOCUMENTS

| | | | | |
|---|---|---|---|---|
| FR | 2579454 A1 * | 10/1986 | | A61F 2/40 |
| WO | WO 0147442 A1 * | 7/2001 | | A61F 2/40 |

*Primary Examiner* — Brian Pellegrino
(74) *Attorney, Agent, or Firm* — Gregory B. Beggs

(57) ABSTRACT

A glenoid implant is disclosed which has a protruding surface on a first side arranged to engage the surface of a cavity formed in a glenoid extending between peripheral glenoid surfaces and a flat surface adjacent the protruding surface of the implant arranged to engage the peripheral glenoid surfaces adjacent the cavity. The implant also has a wear-resistant surface on a second side opposite the flat surface and the protruding surface.

11 Claims, 21 Drawing Sheets

Related U.S. Application Data provisional application No. 60/579,893, filed on Jun. 15, 2004, provisional application No. 60/585,033, filed on Jul. 2, 2004.

(56) References Cited

U.S. PATENT DOCUMENTS

| | | | | |
|---|---|---|---|---|
| 5,376,125 A | * | 12/1994 | Winkler | 623/23.11 |
| 5,723,018 A | * | 3/1998 | Cyprien et al. | 623/19.13 |
| 6,520,995 B2 | * | 2/2003 | Church | 623/22.24 |

\* cited by examiner

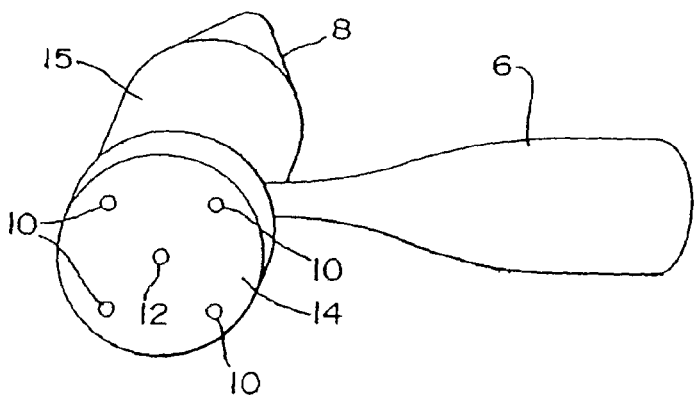
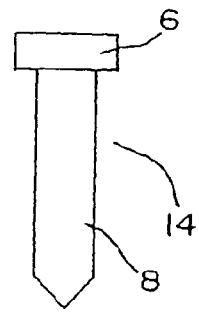
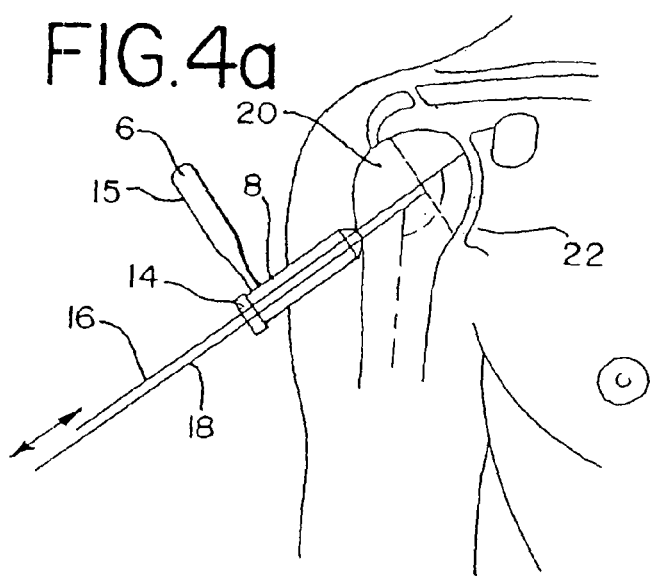
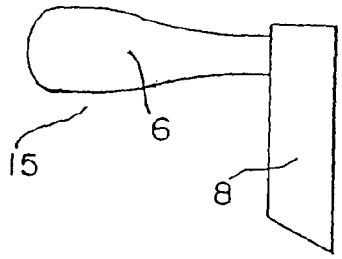
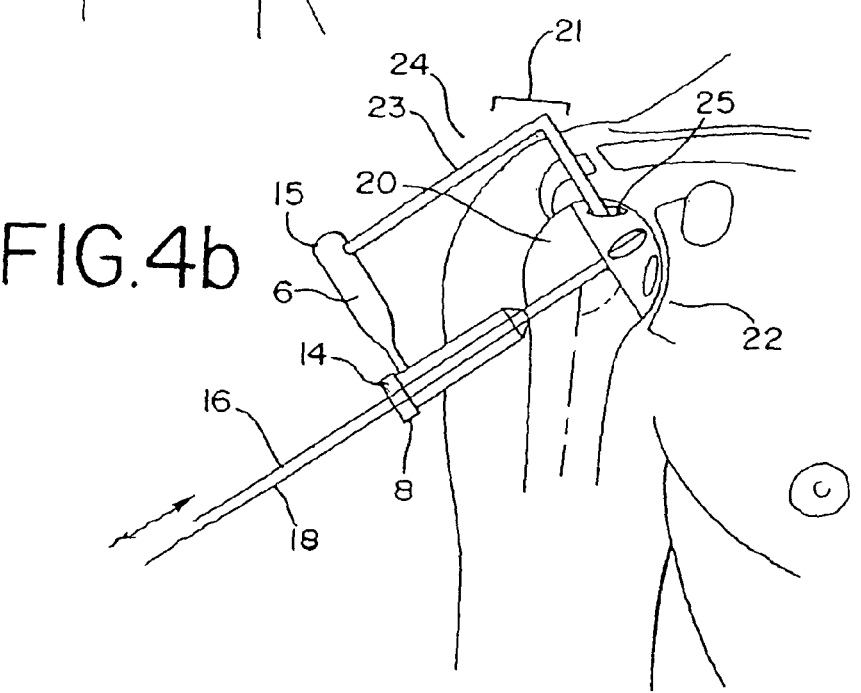

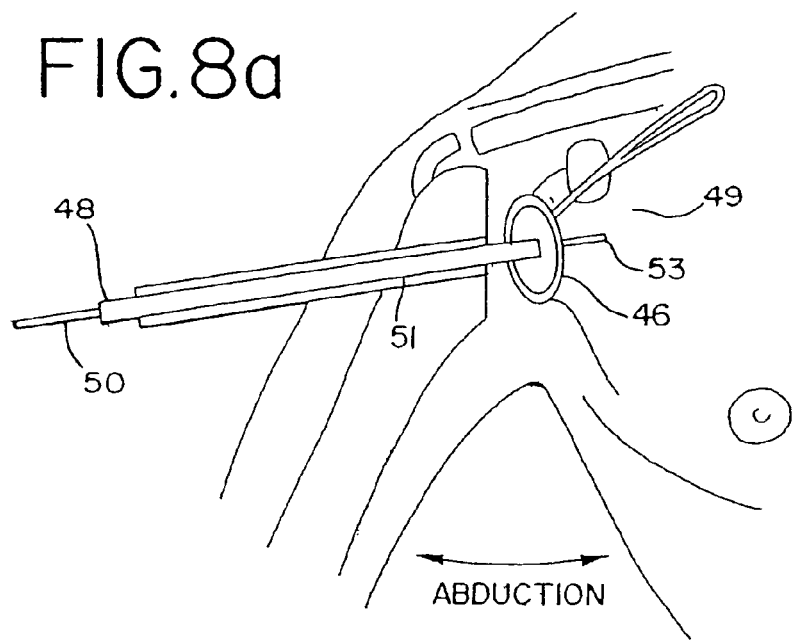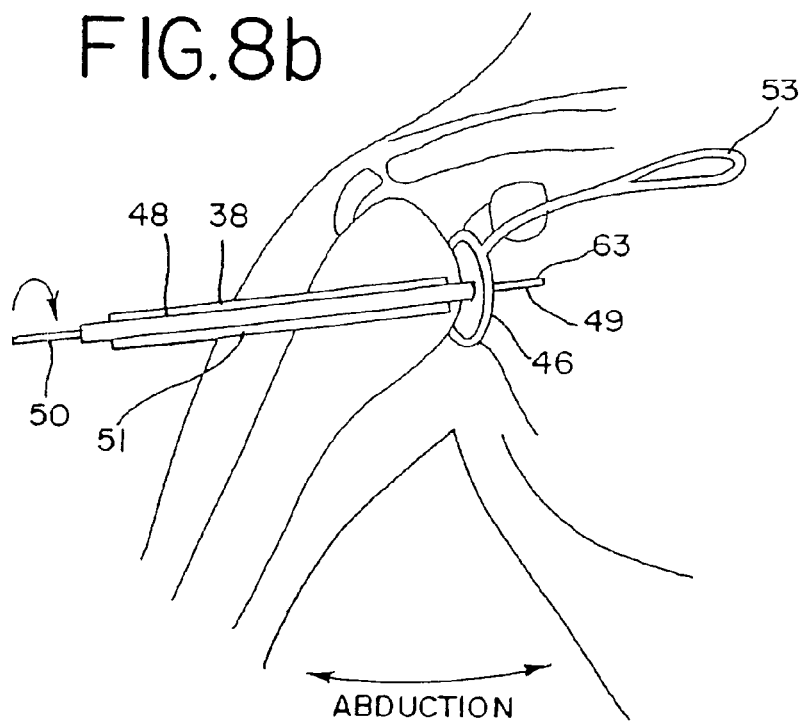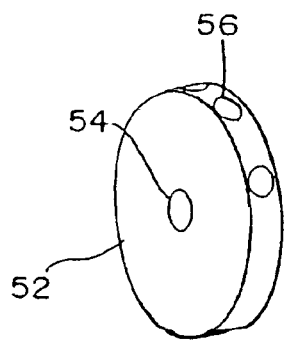

GLENOID IMPLANT FOR MINIMALLY INVASIVE SHOULDER REPLACEMENT SURGERY

CLAIM FOR PRIORITY

This application is a division of application Ser. No. 10/917,266, filed Aug. 11, 2004. As set forth in that parent application, applicant claims, under 35 U.S.C. § 119(e), the benefit of priority of: 1) the filing date of Aug. 11, 2003 of U.S. Provisional Application No. 60/494,289, 2) the filing date of Oct. 8, 2003 of U.S. Provisional Application No. 60/509,655, 3) the filing date of Oct. 16, 2003 of U.S. Provisional Application No. 60/511,805, 4) the filing date of Nov. 19, 2003 of U.S. Provisional Application No. 60/523,401, 5) the filing date of Jun. 15, 2004 of U.S. Provisional Application No, 60/579,893 and 6) the filing date of Jul. 2, 2004 of U.S. Provisional Application No. 60/585,033, the entire contents of each of which, including said parent application, are incorporated herein by reference.

BACKGROUND OF THE INVENTION

1. Field of the Invention

The present invention relates to methods, instrumentation, and implants for orthopaedic surgery and, more specifically, to rotator cuff sparing procedures and associated devices for shoulder replacement surgery.

2. Discussion of Related Art

Orthopaedic surgeons perform joint replacement surgery for patients who suffer pain and physical limitations caused by joint surfaces that have been damaged by degenerative, traumatic, or other pathologic processes. The functional outcome from these joint replacement surgeries is directly related to the degree of morbidity associated with the surgical method and the ability of the method to best restore the natural anatomy and biomechanics of the joint. Orthopaedic surgeons are continually searching for ways to improve outcomes for joint replacement surgery by developing methods of less invasive surgery to limit surgical morbidity and by developing novel methods and implants to better restore the native joint anatomy.

Conventional shoulder replacement surgery has several limitations. It requires an extensive exposure that irreversibly damages the rotator cuff and still fails to gain sufficient joint access to properly restore the native anatomic relationships of both the humeral head and glenoid surfaces. Also, there remain issues with glenoid implant fixation and early loosening.

Conventional methods utilize a large anterior deltopectoral exposure. The anterior humeral circumflex blood vessels are typically ligated and the anterior (subscapularis) musculotendinous unit is transected. The shoulder must then completely dislocated both anteriorly and posteriorly to prepare the humeral and glenoid joint surfaces. This can cause excessive traction on the arm which has resulted in injury to the nerves of the brachial plexus (Lynch N M, Cofield R H, Silbert P L, et al. Neurologic complications after total shoulder arthroplasty. J Shoulder Elbow Surg 1996;5(1):53-61.).

With regards to shoulder replacement surgery, all conventional methods require surgical transection of a rotator cuff tendon to gain sufficient exposure of the joint surfaces of the shoulder (See U.S. Pat. No. 4,550,450, entitled, "Total Shoulder Prosthesis System", the entire contents of which are incorporated herein by reference). After the joint surfaces are replaced, the rotator cuff tendon must be surgically repaired with suture material. This tenuous repair necessitates an obligatory period of approximately six weeks for the rotator cuff tendon to heal before advanced shoulder rehabilitation can be performed. This surgical transection and subsequent repair, as well as the delay in rehabilitation, hold significant consequences for the functional outcome of the shoulder replacement including permanent weakness and decreased range of motion (Miller S L et al., "Loss of subscapularis function after total shoulder replacement: A seldom recognized problem", J Shoulder Elbow Surg. January-February2003; 12(1):29-34).

Additionally, despite the extensive exposure, conventional methods for shoulder replacement surgery still fail to properly restore the native anatomic relationships of the joint surfaces of the shoulder. Conventional methods prepare the humeral surfaces of the shoulder joint by referencing off the intramedullary axis of the humeral shaft. This poses great difficulty for the surgeon since the intramedullary axis has an inconsistent relationship to the humeral surface. The humeral joint surface also possesses a complex anatomy with significant variability which cannot be entirely restored with conventional methods and implants. There exists much variability in the humeral head neck-shaft angle, posterior and medial offset, version (rotation), height, thickness, and radius of curvature. (Boileau P, Walch G, "The Three-Dimensional Geometry of the Proximal humerus", J Bone Joint Surg Br 1997; 79B: 857-865; Iannotti J P, et al. "The Normal Glenohumeral Relationships. An Anatomic Study of One Hundred and Forty Shoulders", J Bone Joint Surg 1992; 74A(4):491-500; McPherson E J, et al. "Anthropometric Study of Normal Glenohumeral Relationships", J Shoulder Elbow Surg 1997;6:105-112; Soslowsky L J, et al. "Articular geometry of the glenohumeral joint", Clin Orthop 1992;285: 181-190). The failure to restore the native anatomic relationships and biomechanics to the shoulder joint has proven to result in a significantly lesser functional and durable outcome (Williams G R, et al. "The effect of articular malposition and shoulder arthroplasty on glenohumeral translations, range of motion, and subacromial impingement", J Shoulder Elbow Surg. 2001; 10(5):399-409).

Conventional methods of shoulder replacement surgery also have difficulty gaining access to the glenoid joint surface. The glenoid surface of the shoulder joint is best prepared by working along an axis perpendicular to its surface. Because the humeral head sits in the way, this is a nearly impossible task with conventional methods. The humeral head has to be partially removed, the subscapularis (anterior shoulder rotator cuff muscle) transected, and the proximal humerus dislocated to even get close to working along this axis. Because of this difficulty, a majority of orthopaedic surgeons still choose not to replace the glenoid surface despite clinically proven results of improved pain relief and function for shoulder replacement surgery when both the humeral and glenoid surfaces are replaced. (Boyd A D, Thomas W H, Scott R D, et al. "Total shoulder arthoplasty versus hemiarthroplasty—indications for glenoid resurfacing", J of Arthroplasty 1990;5(4):329-336; Gartsman G M, Roddey T S, Hammerman S M. J Bone Joint Surg 2000;82A(1):26-34; Edwards T B, Kadakia N R, Boulahia A, et al., "A comparison of hemiarthoplasty and total shoulder arthroplasty in the treatment of primary glenohumeral osteoarthritis: Results of a multicenter study", J Shoulder Elbow Surg 2003; 12(3):207-13; Orfaly R M, Rockwood Calif., Esenyel C Z, et al., "A prospective functional outcome study of shoulder arthoplasty for osteoarthritis with an intact rotator cuff", J Shoulder Elbow Surg 2003;12(3):214-21.)

Despite improved results of conventional methods when both the humerus and glenoid surfaces are replaced, there still remains limitations with regard to glenoid fixation and early glenoid implant loosening (Boileau P, Avidor C, Krishnan S G, et al., "Cemented polyethylene versus uncemented metal-backed glenoid components in total shoulder arthroplasty: a prospective, double-blind, randomized study", J Shoulder Elbow Surg 2002;11(4):351-9.). Both, cemented polyethylene and metal backed glenoid components are used in conventional methods. The cemented implant never incorporates with the glenoid bone and with time, the cement-bone interface eventually fails and the implant comes loose. Conversely, the metal-backed glenoid prosthesis has an unacceptable rate of early loosening, at least 20% in one study. However, if the metal-backed implant can remain rigidly fixed to the bone for a sufficient period of time, the bone of the glenoid will eventually adhere to the metal-backed surface and long-term studies have revealed little evidence for late clinical loosening in these cases. Failure of the metal-backed glenoid implant appears to be related to the limitations in achieving sufficiently rigid and durable initial fixation.

While performing shoulder replacement surgery for arthritis, associated rotator cuff tears are sometimes discovered and should be repaired when possible. If a less invasive surgical approach is employed to perform the shoulder replacement surgery, a less invasive method of rotator cuff repair that is compatible with the method shoulder replacement surgery must be to be available to simultaneously address these associated rotator cuff tears.

BRIEF SUMMARY OF THE INVENTION

One aspect of the present invention regards a method for shoulder replacement surgery. Utilizing the method of the present invention, a portal is created along a central axis of a neck of a proximal humerus that is associated with a shoulder of a patient. An implant is subsequently implanted into the shoulder of the patient, however a component of that implant is not passed through the portal. The rotator cuff is spared in the process.

One advantage provided by the above mentioned aspect of the present invention is that it allows determination of a central axis in the proximal humerus which allows simple and less invasive perpendicular access to the humeral and glenoid joint surfaces. An additional advantage is it offers a simple and reliable means of restoring the native anatomy and biomechanical relationships, allowing for an improved functional and durable outcome.

A further advantage is that it spares the rotator cuff tendons and allows for a quicker and more functional recovery.

Another aspect of the present invention regards a humeral implant with one component that is removably attached to a second component.

Another aspect of the present invention provides a glenoid implant. The glenoid implant includes an ingrowth shell, a wear-resistant surface that is removably attached to the ingrowth shell. An advantage is that the ingrowth shell provides novel geometry and superior fixation to the glenoid.

An additional aspect of the invention regards a transhumeral portal sleeve with a bullet shaped guide that has a central and a peripheral longitudinal cannulation. An advantage is that it safely creates a working portal along the central axis of the proximal humerus.

In another aspect of the present invention, there is provided a transhumeral humeral reamer that has a working head and a removably attached transhumeral shaft with a diameter of from 0.1 to 5 cm.

Another aspect of the present invention regards a transhumeral glenoid reamer with a working head and a removably attached transhumeral shaft that has a diameter of from 0.1 to 5 cm.

In another aspect, a transhumeral protective sheath is provided that is a tube of material with a diameter of from 0.1 to 5 cm.

Another aspect of the invention regards a glenoid surface protective guard that has a protective surface and a removably attached handle.

In another aspect, a humeral head surface protective guard is provided that has a protective surface and a removably attached handle.

An additional aspect of the invention regards a glenoid sizer and centering hole guide that has a surface that contacts the glenoid of a shoulder and a removably attached handle.

In another aspect, a drill guide with a guiding surface and a removably attached handle is provided. The guiding surface has a centering hole and is available in sizes equivalent to the respective glenoid implants.

In another aspect, the invention regards a transhumeral glenoid drill with a working surface and a removably attached shaft.

In another aspect, a transhumeral burr is provided. The transhumeral burr has a high speed working burr surface and a removably attached shaft.

An additional aspect of the invention regards a glenoid keel punch with a working head and a removably attached shaft. The working head has a keel shape and cutting teeth.

In another aspect, a transhumeral irrigation and suction catheter is provided. The catheter is a semi-rigid plastic tubing removably attached to either a fluid pump or a suction device.

In another aspect, a transhumeral cementation device is provided that has a semi-rigid catheter removably attached to a head.

An additional aspect provides a transhumeral glenoid impactor with a dome-shaped head and a removably attached shaft.

Another aspect of the invention regards a transhumeral screw driver with a working head and a removably attached shaft.

In another aspect, the present invention provides a rotator interval retractor with a first blade dimensioned to interact with a supraspinatus and a second blade dimensioned to interact with a subscapularis.

Another aspect of the invention regards a glenohumeral joint with a transhumeral portal along a central axis of a neck of a proximal humerus as well as an implant.

Further advantages as well as details of the present invention ensue from the following description of a preferred embodiment represented in the drawings.

BRIEF DESCRIPTION OF THE DRAWINGS

FIG. 3a is a perspective view of an embodiment of a transhumeral portal drill guide and protective sleeve in accordance with the present invention.

FIG. 3b is a top plan view of the transhumeral portal drill guide of FIG. 3a;

FIG. 3c is a side plan view of the protective sleeve of the transhumeral portal drill guide and sleeve of FIG. 3a in accordance with the present invention;

FIG. 4a is a schematic of an embodiment of an insertion procedure of a proximal humeral guide pin and measurement of humeral head depth-after placement of a second guide pin in accordance with the present invention;

FIG. 4b is a schematic of the insertion of FIG. 4a using an optional embodiment of a radiolucent guide attachment to assist with a guide pin insertion procedure in accordance with the present invention;

FIG. 8a is a schematic showing a possible way of drilling a glenoid centering hole and placing a transhumeral glenoid guide wire with a glenoid sizing and centering guide which can be used for both a left and a right shoulder for a conventional proximal humeral implant in an embodiment of a surgical procedure in accordance with the present invention;

FIG. 8b is a schematic showing a possible way of drilling a glenoid centering hole and placing a transhumeral glenoid guide wire with a glenoid sizing and centering guide which can be used for both a right and a left shoulder for a novel proximal humeral implant during an embodiment of a surgical procedure in accordance with the present invention;

FIG. 8c is a perspective view of an embodiment of a head of a glenoid sizing and centering guide in accordance with the present invention;

FIG. 13b is a perspective view of an embodiment of a modular glenoid cement pressurizer tip for a keel implant and a catheter in accordance with the procedure shown in FIG. 13a;

FIG. 23b is a bottom plan view of a shell component of a novel glenoid implant of FIG. 23a;

FIG. 24b is an exploded view of the glenoid drill guide sleeve interfit with the glenoid screw guide sleeve of FIG. 24a;

FIG. 25b is an exploded view of the glenoid screw guide sleeve of FIG. 25a;

FIG. 26b is an exploded view of the novel glenoid implant of FIG. 26a;

FIG. 27b is a top plan view of an embodiment of a novel wear-resistant surface the novel glenoid implant of FIG. 27a;

DETAILED DESCRIPTION OF THE DRAWINGS AND THE PRESENTLY PREFERRED EMBODIMENTS

Figure 1:
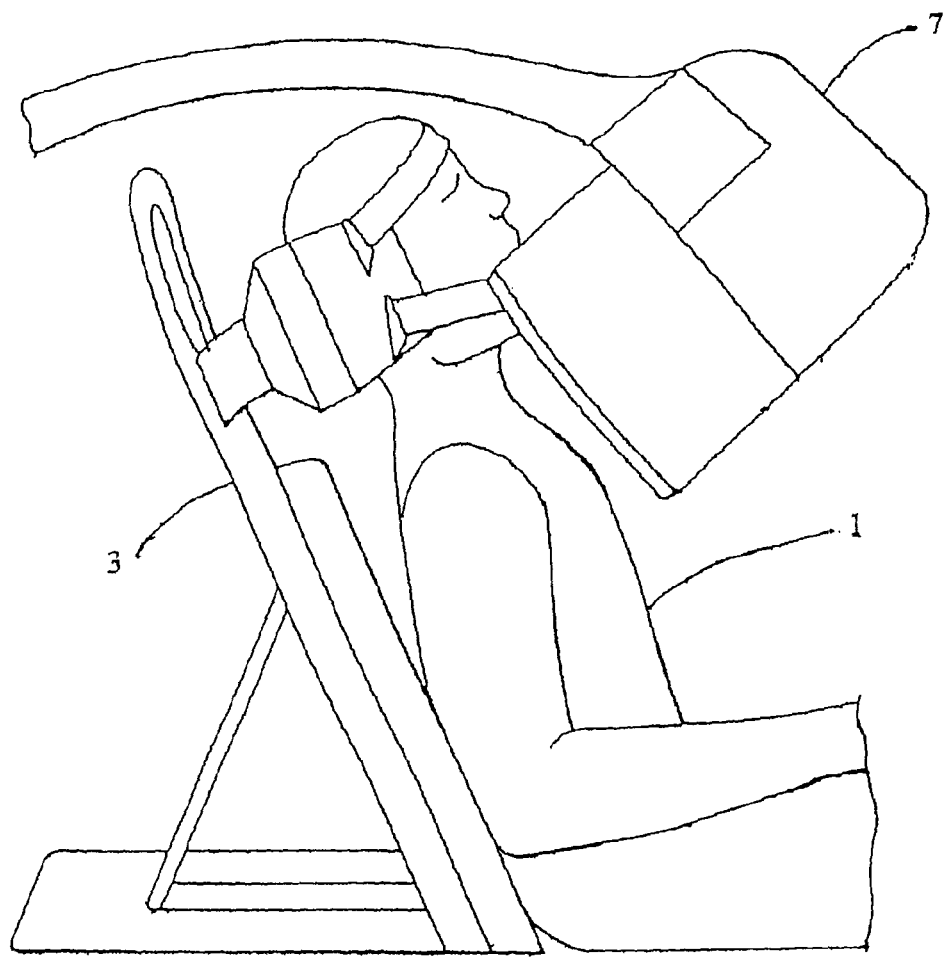
FIG. 1 is a schematic of a patient positioned with fluoroscopy C-arm unit that may be used in conjunction with the present inventions.

The present invention relates to methods, instrumentation, and implants for performing rotator cuff sparing shoulder replacement surgery. Both, total shoulder arthroplasty, where both the humeral and glenoid joint surfaces are replaced, and shoulder hemiarthroplasty, where only the humeral joint surface is replaced, can be performed as indicated. The present invention utilizes among other things: a novel surgical exposure including an optional method of arthroscopic anterior contracture release, posterior capsular tightening, osteophyte resection, and glenoid soft-tissue clearance; two limited incisions, a transhumeral portal and a deep rotator cuff sparing exposure; novel transhumeral instrumentation with modular working components, protective guides, sleeves, sheaths, and retractors; conventional or novel implants, and an associated method of rotator cuff repair.

Utilizing the method of the present invention, a portal is created along a central axis of a neck of a proximal humerus that is associated with a shoulder of a patient. This portal provides superior perpendicular access to both the humeral and glenoid joint surfaces in a less invasive manner to allow more anatomic replacement surgery to occur. The axis of the humeral head and the axis of the glenoid have a sufficiently consistent natural relationship such that simple positioning of the arm can allow a surgeon to easily align the central axis perpendicular to the humeral head with the axis perpendicular to the glenoid. Research has shown that there exists a natural relationship between the orientation of the humeral and glenoid surfaces (De Wilde, L F, et al., "Glenohumeral Relationship in the Transverse Plane of the Body", J Shoulder Elbow Surg 2003;12(3):260-267). Therefore, I have determined that with consistent positioning of the arm, these axes will be co-linear.

Accordingly, the present invention provides a reliable way of reestablishing the proper orientation of the humeral and glenoid joint surfaces without the associated surgical morbidity of conventional methods, i.e., a large exposure, dislocation of the humerus, or transection of the rotator cuff, as will be described below. Note that in the description to follow there will be mention made of transhumeral instruments. Such transhumeral instruments include transhumeral proximal humerus and glenoid reamers, drills, burrs, guides, protective guards, sheaths, sleeves, cementation tools, glenoid peg and keel punches, and glenoid implant insertor and impactor.

Shown in FIGS. 4a-b, 5, 6, 7a-b, 8a-b, 9a-b, 10a-c, 11a-b, 12a-b, 13a, 13e, 14a-b, 16, 17a, 18a-b, 19a, 20a, 22, 24a, 25a, and 26a, is a possible medical procedure according to the present invention. Preoperatively, two orthogonal radiographic images should be taken including a Grashey anteroposterior view with the patient's shoulder held in neutral rotation to slight external rotation and an axiliary lateral view. Next, two-dimensional transparencies with representations of different sizes of the humeral and glenoid implants/templates are placed over the x-rays to evaluate the patients bony anatomy and estimate the size of the implants to be used. From these radiographic images, preoperative measurements can be taken of the humeral head diameter and depth, the humeral neck angle, glenoid size and version, and the amount of scapular bone available to fix the implants to be used in the surgical procedure. A preoperative CT scan of the shoulder can also be useful when plain radiographs do not offer sufficient detail.

After interscalene regional block and general anesthesia are administered by the anesthesiologist, the patient 1 is positioned in a sitting position with a beach chair positioner 3 as shown in FIG. 1. Prior to prepping and draping the patient 1, a fluoroscopic C-arm machine 7 is positioned accordingly to the patient 1 to obtain a Grashey anteroposterior radiographic view and a modified axiliary lateral view using rotation of the shoulder and slight repositioning of the fluoroscopic machine 7. After the fluoroscopic views are confirmed, the fluoroscopic machine 7 is backed away from the patient 1 and the shoulder and upper extremity are prepped and draped in sterile fashion.

Initially, an optional arthroscopic procedure may be performed using conventional arthroscopic tools to release the anterior capsular contractures, tighten the posterior capsule, resect osteophytes, and clear the glenoid soft-tissue for exposure. The procedure is begun by placing an arthroscope in the shoulder joint through a standard posterior portal and making an anterior rotator interval passage under needle localization. Standard diagnostic arthroscopy is performed and the posterosuperior, superior, and anterior labrum are excised or ablated; the biceps tendon may be released from the superior glenoid; and the anterior and anteroinferior ligamentous and capsular attachments are released from the glenoid. Then an accessory posterior passage is made under needle localization and an arthroscopic burr is inserted to remove the inferior humeral neck osteophytes. From the same accessory posterior passage, the posterior, posteroinferior and inferior labrum are excised or ablated and the posteroinferior and inferior ligamentous and capsular attachments to the glenoid are released from 7 O'clock anteriorly on a right shoulder or 5 O'clock anteriorly on a left shoulder. Gentle manipulation of the shoulder can also be performed if necessary to complete the soft-tissue release. Any posterior capsular redundancy can be addressed by techniques of capsular plication (tightening with arthroscopic sutures).

Figure 2A:
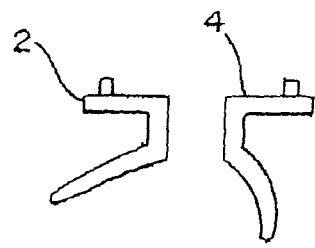
FIGS. 2a and b are plan views of an embodiment of a rotator interval retractor with specialized supraspinatus and subscapularis blades (FIG. 2b) in accordance with the present invention.
Figure 2B:
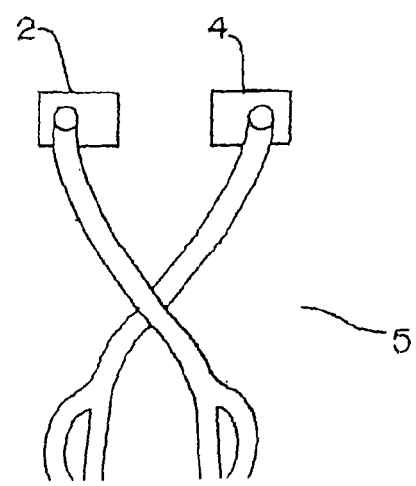

After the optional arthroscopic procedure is performed, an anterosuperior passage is formed to expose the glenohumeral joint. In particular, an anterosuperior incision is made either obliquely running over the anterolateral border of the acromion over the tip of the coracoid or longitudinally from just inferior to the clavicle running between the coracoid and the AC joint distally. Deep dissection is continued through the deltopectoral interval or a limited muscular split running in line with the deltoid muscle fibers. The clavipectoral fascia is incised, the coracoacromial ligament is released from the coracoid, and the subdeltoid and subacromial adhesions are released. Bony and soft-tissue subacromial decompression and distal clavicle excision should be performed if secondary conditions of impingement, rotator cuff tears, or acromioclavicular joint arthritis are present. The anterior circumflex blood vessels are ligated only as needed. The rotator interval is opened completely around both sides of the coracoid and distally into the biceps sheath. The supraspinatus and subscapularis muscles are bluntly released from the glenoid superior and anterior surfaces, respectively. A biceps tenodesis may be performed by simply sewing it to the tissue of the biceps sheath and excising the intraarticular portion of the tendon. At this point, a novel rotator interval retractor 5 with specialized supraspinatus 2 and subscapularis 4 blades is inserted (FIGS. 2a-b). The blades connect to separate arms of a self-retaining device which allow it to hold open the interval between the supraspinatus and the subscapularis rotator cuff musculotendinous units.

If necessary, a secondary rotator interval can be made by splitting the subscapularis in line with its fibers.

Note, that the anterosuperior passage described above and below can be performed without the aid of the previously described arthroscopic procedure. If the arthroscopic procedure is not performed, joint capsular contractures are released, posterior capsule is tightened (if needed), osteophytes are resected, and the soft-tissue surrounding the glenoid is excised as described above using open rather than arthroscopic instruments.

The surgical method next involves creating a transhumeral portal 30. The transhumeral portal 30 is a cylindrical-like tunnel that is parallel to the neck of the humerus from the anterolateral bony cortex of the proximal humerus through the center of the humeral head. Creation of the transhumeral portal 30 first involves obtaining an anteroposterior view of the proximal humerus via the fluoroscopic C-arm machine 7 shown in FIG. 1. The shoulder is externally rotated between 20 and 40 degrees relative to the plane of the fluoroscope 7 to achieve a view perpendicular to the neck of the humerus. A free radioopaque guide pin is placed over the anterior shoulder along the axis of the humerus neck. By using fluoroscopy, a guide pin in that position defines a line to be used as a guideline that is marked/drawn along the anterior skin. A second small anterosuperior incision is made longitudinally, 1 centimeter lateral to the biceps tendon centered on the point of intersection with the drawn guideline marking the humeral neck axis. This second incision lies just inferolateral to the first. Via the second anterosuperior path, the deep deltoid muscle is split bluntly along its fibers to protect the motor branch of the axillary nerve and the transhumeral portal drill guide 14 and protective sleeve 15 (FIGS. 3a-c) are inserted down to the anterolateral cortex of the humerus, approximately 1 cm lateral to the biceps groove. Using intraoperative fluoroscopy, a small guide pin 16 is inserted through the transhumeral portal drill guide 14 and sleeve 15 from the anterolateral humeral cortex along the central axis of the humeral neck into the center of the articular surface of the humeral head (FIG. 4a). Anteroposterior and modified axillary lateral fluoroscopic images are taken to confirm proper positioning of the guide pin 16. The guide pin 16 is repositioned as necessary until the pin runs centrally through the humeral neck and head on all fluoroscopic views.

Note, a specialized transhumeral portal drill guide 14 may be used to help direct the guide pin 16 into the center of the humeral head 20 (FIG. 4a). The transhumeral portal drill guide 14 is a bullet shaped object with multiple longitudinal cannulations to direct guide 16, 18 . It fits into a protective sleeve 15 which has a handle 6 that is inserted into the second anterosuperior passage to the anterolateral cortex of the proximal humerus 20. This sleeve 15 and guide 14 protect the surrounding soft-tissue and axillary nerve from harm. There is a radiolucent guide attachment 21 which rigidly connects to the handle 6 of the protective sleeve 15 of the transhumeral portal drill guide 14. The radiolucent guide attachment 21 has a radiolucent arm 23 which runs parallel with the cannulations 10,12 in the transhumeral portal guide 14 and connects to a radiolucent tip 25 which can be any suitable shape, for example, hemispheric (FIG. 4b). Once the guide is assembled, the central cannulation 12 of the transhumeral portal guide 14 will direct a guide pin 16 to the center of the hemispheric tip 25. The arm 23 of the guide attachment 21 is sufficiently long to allow significant adjustments in length to accommodate variations in size of the proximal humerus. After the tip 25 of the transhumeral portal drill guide 14 is placed on the humeral surface through the first anterosuperior passage, the radiolucent arm 23 containing a radiopaque reference line can also be aligned with the central axis of the neck of the proximal humerus 20 under fluoroscopy to assist in directing the guide pin 16 to the center of the humeral 20 surface.

The guide pin 16 is advanced through the transhumeral drill guide 14 and protective sleeve 15 such that it travels toward the glenohumeral joint 9, along the central axis of the neck of the humerus and perpendicular to the humeral 20 joint surface. The guide pin 16 is advanced such that the tip of the pin stops right at the humeral 20 joint surface. A second pin 18 of equal length is inserted through one of the peripheral holes 10 in the transhumeral portal drill guide 14 and sleeve 15 until it stops at the lateral humeral cortex. Measuring the difference in exposed length between the pins 16,18 closely estimates the length of the transhumeral portal 30. This measurement assists the surgeon in creating and using the transhumeral portal 30 more safely as well as providing the size of the modular stem 98 used for the proximal humeral implant 94. Then, the second guide pin 18 is advanced into the bone until it reaches the level of the anatomic neck 13 of the humerus. Measuring the difference in exposed length between the pins 16, 18 provides an accurate measurement of humeral head 20 depth (FIGS. 4a-b). Using the actual humeral depth measured by the difference between the pins, 16, 18 and that measured on the fluoroscopic screen, the actual humeral head diameter can be determined from measurements on the fluoroscopic screen. These measurements help in selecting the proper size transhumeral humeral reamers and final humeral implant later in the procedure.

Figure 5:
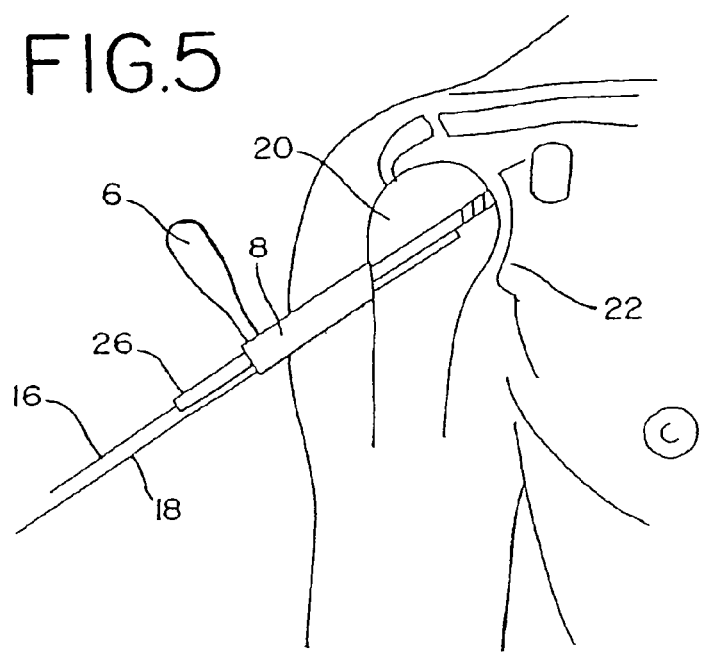
FIG. 5 is a schematic of an embodiment of a drilling procedure for forming an embodiment of a transhumeral portal in accordance with the present invention.

Based on the actual measured transhumeral portal 30 length, the transhumeral portal 30 is created by drilling with an approximately 1 centimeter diameter or less cannulated drill bit 26 through the transhumeral portal protective sleeve 15 over the first guide pin 16 from the anterolateral humeral cortex and into the joint (FIG. 5). The transhumeral portal 30 defines an opening of any suitable shape (such as circular, square, triangular, etc), having a diameter with a range of 0.1 to 5 cm, more preferably, a range of 0.1 to 1 cm, and most preferably, a range of 0.5 to 1.0 cm. The first guide pin 16 is removed along with the cannulated drill bit 26 and the second guide pin 18 may remain as a guide for later humeral head resection.

With the formation of the transhumeral portal 30, the humeral 20 and glenoid 22 surfaces can be prepared as explained hereafter. Note that the order of preparing either the humeral 20 or glenoid 22 surfaces may be altered depending on the proximal humeral 20 bone quality. If there are concerns about the quality of the proximal humeral 20 bone, the humeral 20 surface can be prepared last, after the glenoid 22, to avoid weakening the proximal humeral bone 20 and jeopardizing the integrity of the transhumeral portal 30. Also, if hemiarthroplasty is indicated, the humeral 20 surface may solely be prepared and replaced.

Figure 6:
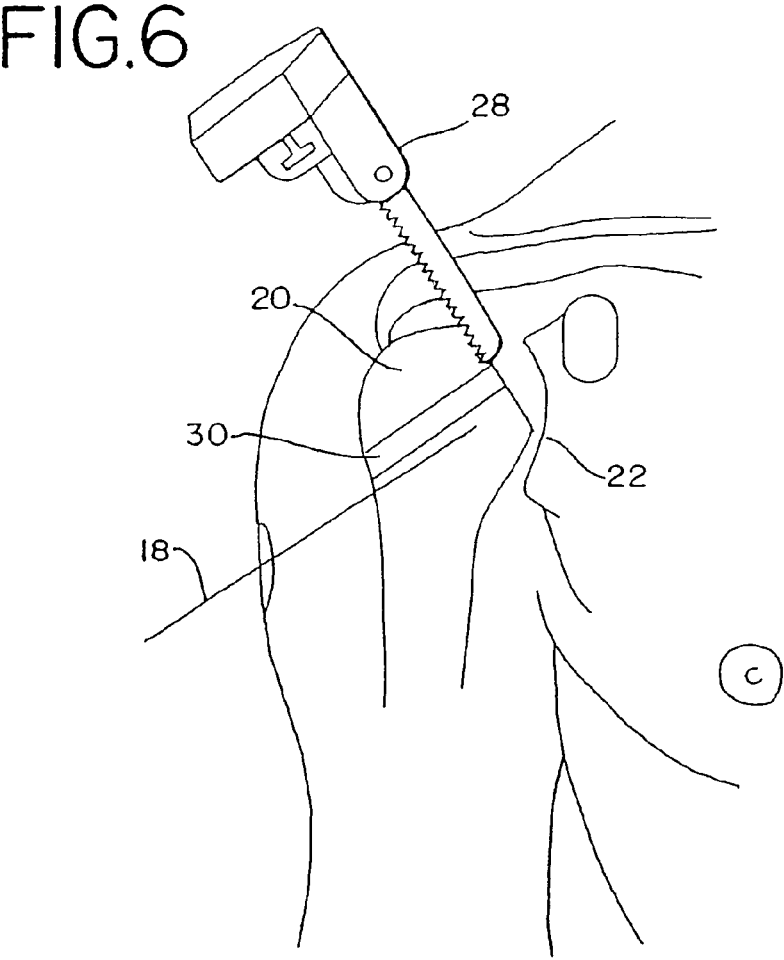
FIG. 6 is a schematic of a preliminary cut of a humeral head joint surface during an embodiment of a surgical procedure in accordance with the present invention.

Assuming that it is determined to prepare the humeral 20 surface first, the articular surface of the humeral head 20 may either be resected and replaced to the level of the anatomic neck 13 for the insertion of a conventional proximal humeral implant, or merely resected and replaced to the level of the subchondral bone for the insertion of a novel proximal humeral implant 94. To insert a conventional humeral implant in accordance with the present invention, a preliminary humeral head 20 cut can be made to improve visualization and expedite resection. From the anterosuperior passage previously formed, a long oscillating saw 28 is used to safely resect a limited portion of the humeral head 20 joint surface perpendicular to the portal (FIG. 6).

Figure 7A:
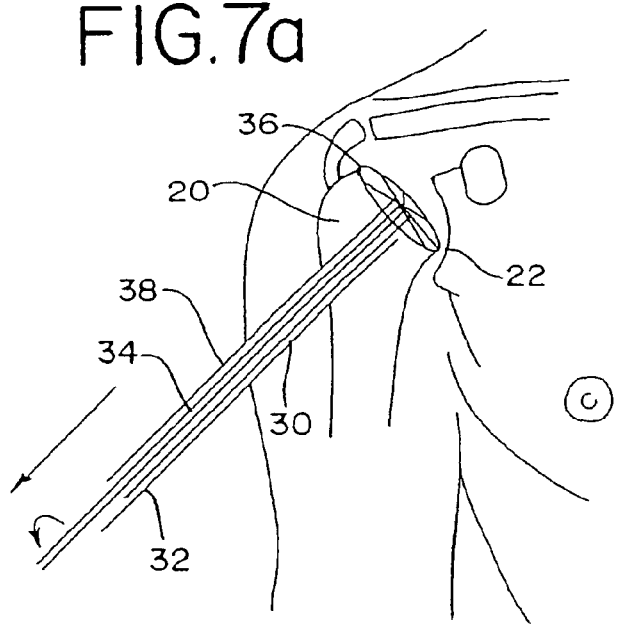
FIG. 7a is a schematic showing a possible way of preparing the humeral head with a transhumeral humeral head reamer in preparation for a conventional proximal humeral implant during an embodiment of a surgical procedure in accordance with the present invention.

A transhumeral protective sheath 38 used during the procedure of the present invention is then threaded or press-fit into the transhumeral portal 30 through the second anterosuperior passage using the transhumeral portal drill guide protective sleeve 15 to safely direct it. It is inserted to the level of the anatomic neck 13 of the proximal humerus 20 in preparation for a conventional humeral implant or to the level of the humeral 20 joint surface for a novel humeral implant 94 (FIG. 7a). An embodiment of the transhumeral protective sheath 38 of the present invention provides protection for the bone within which the transhumeral portal sits. The transhumeral sheath 38 is a tube of such shape, inner and outer diameter, and thickness such that it interfits securely within the transhumeral portal 30 along the central axis of the neck of the humerus 20, allows easy passage and use of all transhumeral instruments and sleeves while protecting the remaining bone of the proximal humerus 20 from harm. The transhumeral sheath 38 may be metal, plastic, or other semi-rigid, wear-resistant material and may be slid or threaded into the transhumeral portal.

Figure 7B:
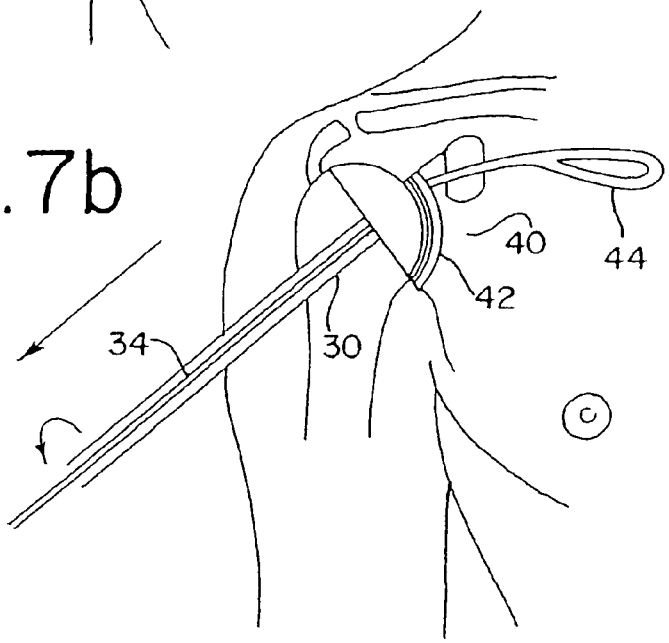
FIG. 7b is a schematic showing a possible way of preparing the humeral head with a novel transhumeral humeral reamer in preparation for a novel proximal humeral implant during an embodiment of a surgical procedure in accordance with the present invention.
Figure 7C:
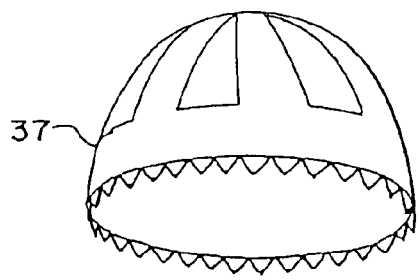
FIG. 7c is a perspective view of an embodiment of a novel transhumeral humeral reamer head to be used in an embodiment of a surgical technique in accordance with the present invention.

Next, a transhumeral reamer shaft 34 is placed through the protective sheath 38 and assembled in the joint with the appropriately sized modular humeral reamer head 36 inserted through the anterosuperior passage (FIGS. 7a-d). A novel transhumeral humeral reamer 32, in one embodiment of the present invention, includes a reaming surface 36 and a transhumeral shaft 34. The transhumeral reamer 32 is designed so that the shaft 34 interfits securely within the transhumeral portal 30, and more specifically, within the transhumeral protective sheath 38 within the transhumeral portal 30, such that there is no shaking or toggling while the reamer is being used. Therefore the diameter of the shaft 34 is from 0.1 to 5 cm and slightly smaller than the inner diameter of the transhumeral protective sheath 38 through which it traverses. For a conventional humeral prosthesis, a flat reaming head surface 36 with sizes similar to the diameter of the humerus and surgical neck are used. The flat reamer removes bone of the humeral head down to the level of the anatomic neck 13 of the humerus. For a novel humeral implant 94, a hemispherically shaped reaming surface 37, sized similarly to a novel humeral surface 96 implant component is used, having similar depth and radius of curvature (FIG. 7*c*). The hemispherically shaped reaming surface 37 removes a minimal amount of bone. The amount of bone removed is roughly equivalent to the thickness of the humeral surface 96 component of the implant 94.

Figure 7D:
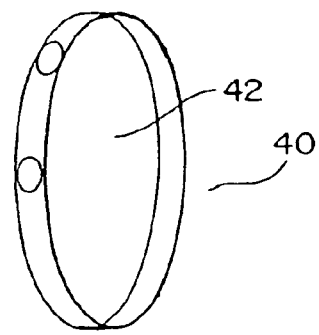
FIG. 7d is a perspective view of an embodiment of a glenoid protective cap to be used in an embodiment of a surgical technique in accordance with the present invention.

A protective guard 40 may be placed over the glenoid through the anterosuperior passage during reaming (FIG. 7*d*). The protective guard 40 is introduced through the first anterosuperior passage by a handle 44. In one embodiment of the present invention, the guard 40 is shaped like the glenoid and is available in small, medium and large sizes. The guard is made of a solid metal surface with an elevated peripheral edge that fits over the glenoid surface. The guard has a thickness of about 0.1 to 2 mm. The handle 44 is removable and can be attached to the guard at different positions to allow it to be inserted from variable angles through the anterosuperior passage.

After the guard 40 is in place, the orthopaedic surgeon grasps the protective sheath 38 and pulls the running reamer 32 back onto the humeral head until it cuts to the level of the anatomic neck 13 for a conventional humeral implant (FIG. 7*a*). Live fluoroscopy may be used to assist with making the cut and insuring that the reamer stays parallel to the second guide pin 18 and stops before its tip. The bone debris from the cutting is removed with thorough irrigation from the anterosuperior passage. Any remaining humeral osteophytes may be removed with a small rongeur from the anterosuperior passage.

To insert a novel proximal humeral implant 94, the transhumeral protective sheath 38 and reamer shaft 34 are inserted as described above (FIGS. 7*a-d*). Alternatively, the appropriate size novel modular humeral reamer head 37 is inserted through the anterosuperior passage into the joint and assembled with the transhumeral shaft 34. A protective guard 40 may be placed over the glenoid 22 through the anterosuperior passage during reaming. Again, the orthopaedic surgeon grasps the protective sheath 38 and pulls the running reamer 32 back onto the humeral head until the novel humeral reamer has removed just enough bone to restore the proper humeral head dimensions (FIG. 7*b*). Openings 39 in the reamer head can help the surgeon determine the proper amount reaming. Also, live fluoroscopy may be used to assist with making the cut and insuring that the reamer 32 stays parallel to the second guide pin 18 and stops at the appropriate level. The bone debris from the cutting is removed with thorough irrigation and suction from the anterosuperior passage. Any remaining humeral osteophytes may be removed with a small rongeur from the anterosuperior passage.

After the reamer 32 has prepared the humeral head, either for a conventional or a novel proximal humeral implant 94, the glenoid 22 of the shoulder joint can then prepared for the placement of a conventional glenoid implant 115 (FIG. 8*a*). Any remaining soft-tissue obstructing the glenoid surface 22 should be excised. The humerus is abducted, rotated, and laterally distracted to direct the transhumeral portal 30 such that its path lies perpendicular to and centered on the glenoid surface 22. A glenoid sizing and centering hole guide 46 is placed from the anterosuperior passage (FIGS. 8*a-c*). In another embodiment of the present invention, a glenoid sizer and centering hole guide 46 includes a working surface 52 and a handle 53. The guide 46 is shaped and sized according to the shape and size of the glenoid 22 to be prepared. The working surface 52 is inserted through the first anterosuperior passage by its handle 53. The handle 53 is removable and can be attached to the working surface 52 at different positions 56 to allow it to be inserted from variable angles through the anterosuperior passage. The working surface 52 is approximately 0.1 to 10 mm thick and flat and has a central hole 54.

Utilizing the appropriately sized glenoid sizing and centering guide 46, a transhumeral guide wire 50 is inserted into the transhumeral portal 30 through the transhumeral protective sheath 38 to drill a centering hole in the glenoid surface 22 regardless of whether a conventional or novel humeral implant is being inserted (FIGS. 8*a-b*). After the centering hole has been started, the guide wire 50 is backed up to allow the removal of the glenoid sizing and centering guide 46. A cannulated flat or hemispherical humeral head guard 64, followed by a cannulated glenoid surface cutting reamer head 60, is inserted through the anterosuperior passage and the guidewire 50 is advanced through cannulations in both instruments back into the centering hole in the glenoid.

Figure 9A:
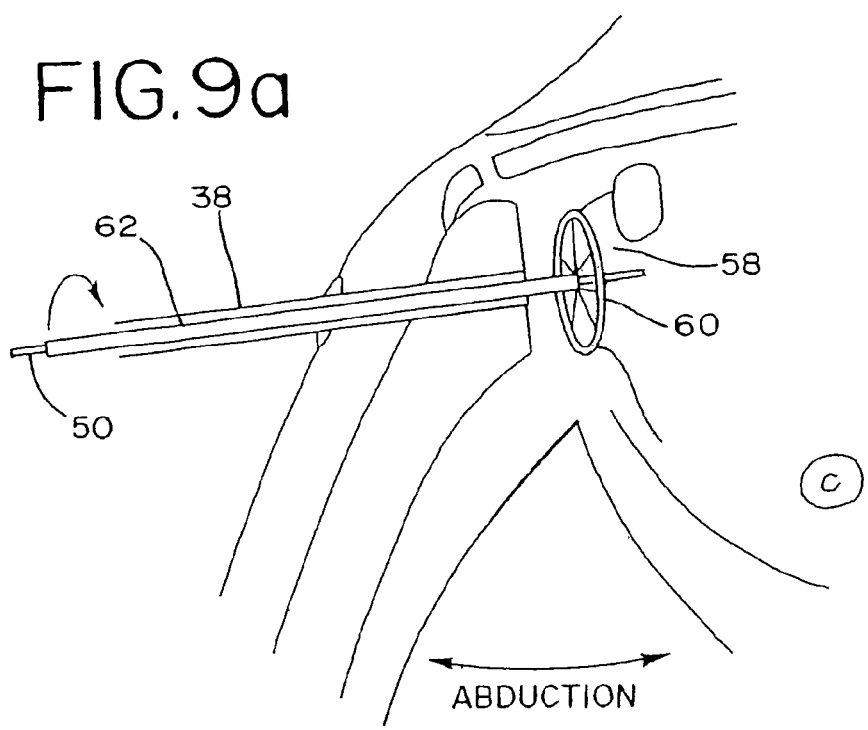
FIG. 9a is a schematic of a way of preparing a glenoid with a cannulated transhumeral glenoid reamer for conventional proximal humeral implant during an embodiment of a surgical technique in accordance with the present invention.
Figure 9B:
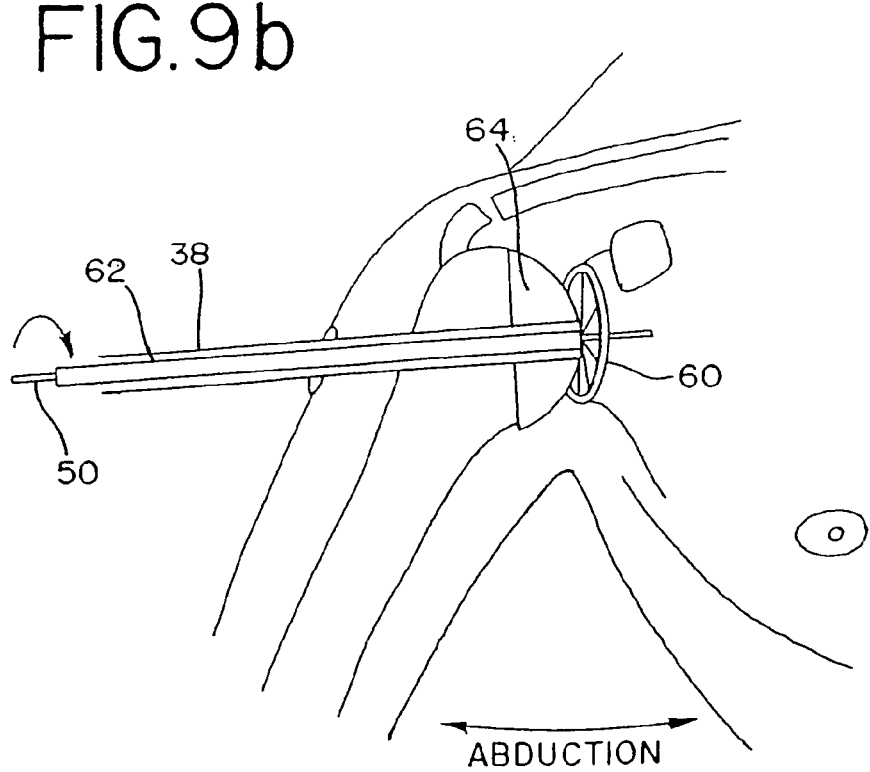
FIG. 9b is a schematic of a way of preparing a glenoid with a cannulated transhumeral glenoid reamer for a novel proximal humeral implant during an embodiment of a surgical technique in accordance with the present invention.

In another embodiment of the present invention, a humeral head surface protective guard 64 may be used (FIGS. 9*a-b*). This protective guard 64 includes a protective metal surface which is flat or hemispheric in shape corresponding to the prepared end of the proximal humerus for a conventional or novel humeral implant, respectively. The protective guard 64 is inserted via the first anterosuperior passage and fits over the humeral surface 20 and the shaft 62 of the transhumeral glenoid reamer 58. The shaft 62 of the transhumeral glenoid reamer 58, described below, passes through a central cannulation of the guard 64 to prepare the glenoid 22. The humeral head surface protective guard 64 is sized according to need, such as small, medium, and large. The guard 64 is approximately 0.1 to 2.0 mm thick. Optionally, the guard 64 may be used with a handle.

The present invention also provides a transhumeral glenoid reamer 58 (FIGS. 9*a-b*, 21, 22, 23*a-b*). The glenoid reamer 58 has a shaft 62 and a working head 60. The shaft 62 is designed to interfit securely within the transhumeral portal 30, and more specifically, within the transhumeral protective sheath 38 within the transhumeral portal 30, such that there is no shaking or toggling of the shaft 62 within the transhumeral portal 30 while the transhumeral glenoid reamer 58 is in use. Therefore, the outer diameter of the shaft 62 is approximately 0.1 to 5 cm, and slightly less than the inner diameter of the transhumeral protective sheath 38 within which the shaft 62 is used. The working glenoid reamer heads 60, 61 and shaft 62 are cannulated to fit over a central glenoid guide wire 50. There is also a non-cannulated reamer head with a leading central peg which can fit into a central glenoid hole and allow some redirection of the reamer as necessary.

For a conventional glenoid implant 115 (shown in FIG. 14*a*), a nearly flat, slightly convex, reaming head surface 60 is used with sizes being similar to that of a glenoid. The radius of curvature of the reamer surface matches that of the non-articular side of the conventional glenoid implant. The flat reaming head 60 removes a minimal thickness of bone. The same flat reaming head 60 as used for a conventional glenoid implant 115 may also be used before inserting the multiple pegged glenoid implant 117.

Figure 23A:
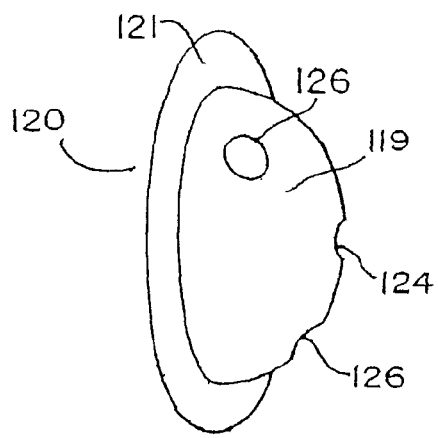
FIG. 23a is a perspective view of an embodiment of a shell component of a novel glenoid implant in accordance with the present invention.
Figure 23B:
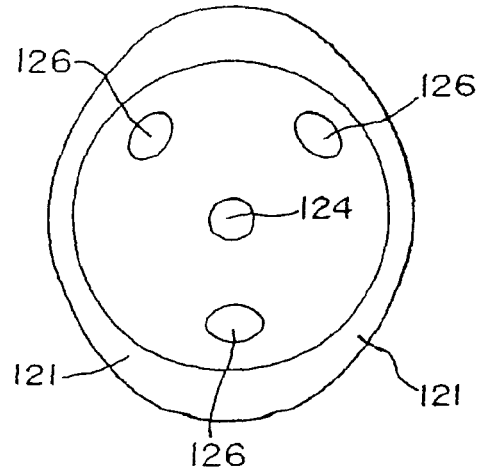

For a novel glenoid implant 118, the glenoid reamer head 61 includes a peripherally flat, less aggressive surface 116 and a centrally raised surface 114 which has a more aggressive reaming surface (FIG. 23*a-b*). The centrally raised surface 114 may be a convex dome, a square, triangle, pyramid, or any other shape that matches the protruding surface of the novel glenoid implant 118 to be implanted within the glenoid, as described below. The peripheral glenoid reaming surface 116 removes a minimal amount of bone from the peripheral surface of the glenoid to just correct the version (orientation) of the glenoid surface. In one embodiment, the central reaming surface 114 removes a spherically shaped area of bone such that a central concave glenoid surface is created which fits an ingrowth shell component 120 of a novel glenoid implant 118 in accordance with the present invention. The concavity is slightly undersized to allow a pressfit of the ingrowth shell 120.

To prepare the glenoid 22 for a conventional prosthesis 115, the cannulated transhumeral glenoid reamer shaft 62 is positioned over the guidewire 50 and through the transhumeral protective sheath 38 from the second anterosuperior passage. The transhumeral reamer shaft 62 is assembled in the shoulder joint with its glenoid surface cutting reamer head 60 and the reamer 58 is advanced along the guide wire 50 removing as little bone as possible to correct the profile of the worn glenoid 22 and create the proper radius of curvature on the surface to match that of the non-articular surface of the conventional glenoid implant 115. The guide wire 50 must be inserted initially in the proper orientation to direct the cut appropriately. There is also an optional glenoid cutting surface head with a central peg that can be used without the guidewire 50 and can be inserted directly into the glenoid centering hole while the surgeon runs the transhumeral glenoid reamer 58 (FIG. 9*a, b*). The bone debris from the cutting is removed with thorough irrigation from the anterosuperior passage. Any remaining glenoid osteophytes may be removed with a small rongeur from the anterosuperior passage.

Figure 10A:
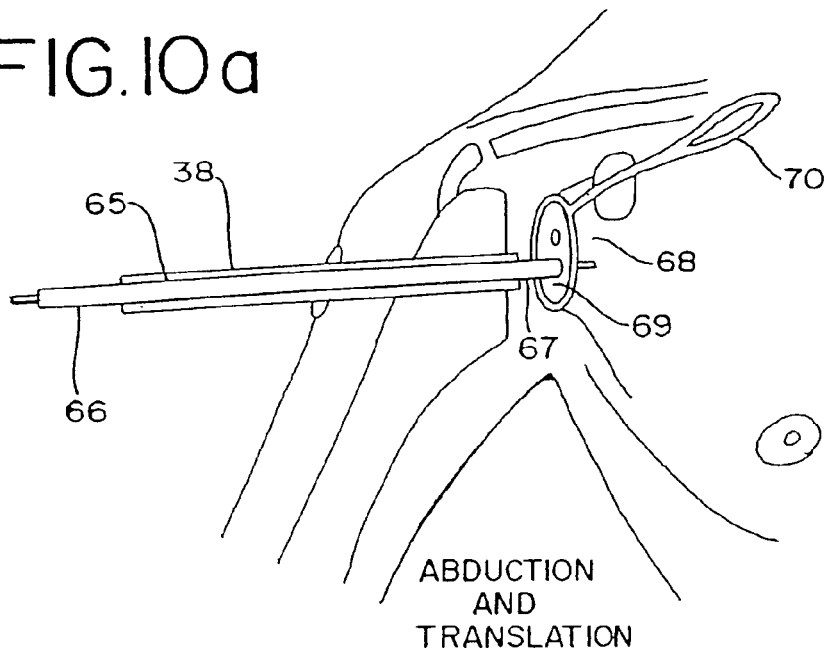
FIG. 10a is a schematic of a way of preparing a glenoid with a transhumeral glenoid keel/peg drill and a glenoid peg or keel guide for a conventional proximal humeral implant during an embodiment of a surgical technique in accordance with the present invention.
Figure 10B:
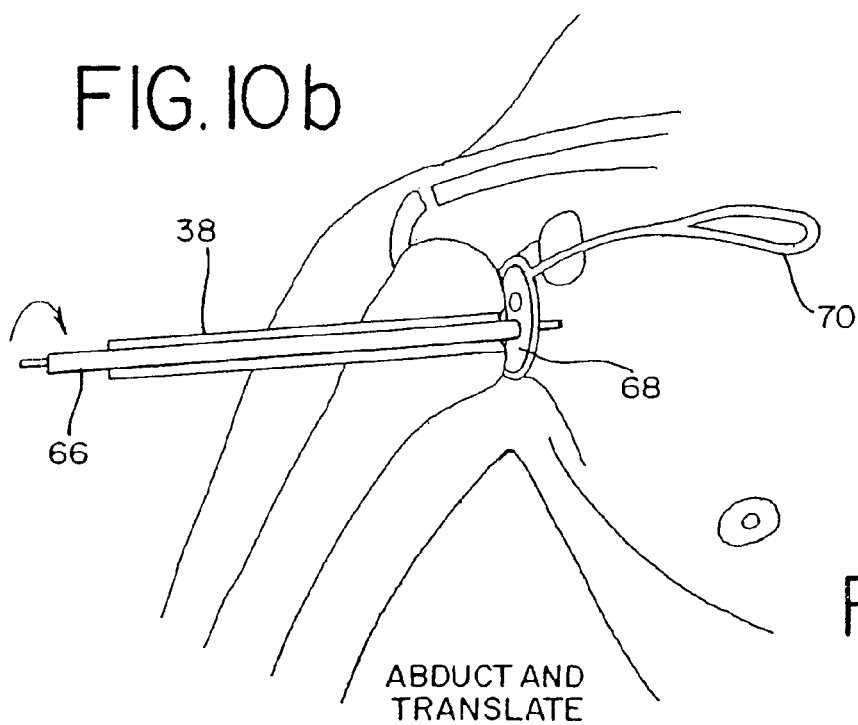
FIG. 10b is a perspective view of a peg or keel guide for a conventional glenoid implant to be used in an embodiment of a surgical technique in accordance with the present invention.
Figure 20B:
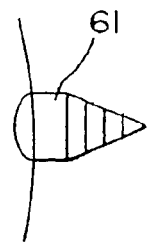
FIG. 20b is a side plan view of a glenoid peg to be used in during a surgical technique in accordance with the present invention.

The glenoid 22 can be prepared for implantation of either a conventional pegged or keeled glenoid implant 115, a multiple peg glenoid implant 117 (FIG. 20*b*), or a novel glenoid implant 118. In the case of implanting a conventional peg or keel glenoid implant 115, the appropriately sized (according to the previously used glenoid sizer and centering hole guide), peg glenoid or keel guide 68 is inserted through the anterosuperior passage and centered by placing its peg 72 into the previously created glenoid centering hole (FIG. 10*a*). The transhumeral glenoid drill 66 is placed through the transhumeral protective sheath 38 within the transhumeral portal 30 from the second anterosuperior passage. In one embodiment of the present invention, a glenoid keel drill guide 68 has a working surface 69 and a handle 70. The working surface 69 is introduced via the first anterosuperior passage by its handle 70. The handle 70 is removable and can be attached to the guide 68 at different positions to allow it to be inserted from variable angles through the anterosuperior passage. This drill guide 68 is shaped and sized similarly to the glenoid sizing and centering hole guide 46, discussed above. The working surface 69 of the guide 68 has a central peg 72 that fits into a centering hole in the glenoid bone. The drill guide 68 for the conventional keel glenoid implant has two converging holes, one superior and one inferior, directed toward each other to direct a transhumeral glenoid drill 66 to cut a keel shape into the glenoid bone (FIG. 10*b*).

The previously mentioned glenoid peg drill guide 68 has a working surface 69 and a handle 70. The working surface 69 is inserted through the first anterosuperior passage by its handle 70. The handle 70 is removable and can be attached to the guide surface 69 at different positions to allow it to be inserted from variable angles through the anterosuperior passage. This drill guide 68 is sized and shaped similarly to the glenoid sizing and centering hole guide 46, discussed above. The working surface 69 of the guide 68 has a central peg 72 that fits into a centering hole in the glenoid bone. The working surface is approximately 0.1 to 5 mm thick and has peripheral holes in parallel configuration to drill holes with a transhumeral glenoid drill 66 for pegs in a glenoid.

In one embodiment, the above-mentioned transhumeral keel/peg glenoid drill 66 has a working surface 67 and a removably attached transhumeral shaft 65. The working surface 67 is a drill bit (or tip) for drilling holes in the glenoid for keels or pegs of the conventional glenoid implant 115. The drill bit 67 (or tip) is larger for drilling holes for a keel or a peg than a bit used for drilling holes for screws.

Figure 10C:
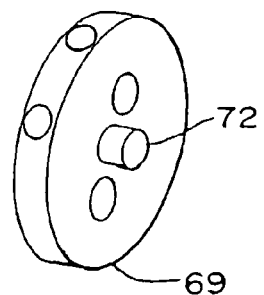
FIG. 10c is a schematic of a way of preparing a glenoid with a transhumeral keel/peg glenoid drill and a glenoid peg or keel guide for a novel proximal humeral implant during an embodiment of a surgical technique in accordance with the present invention.
Figure 11A:
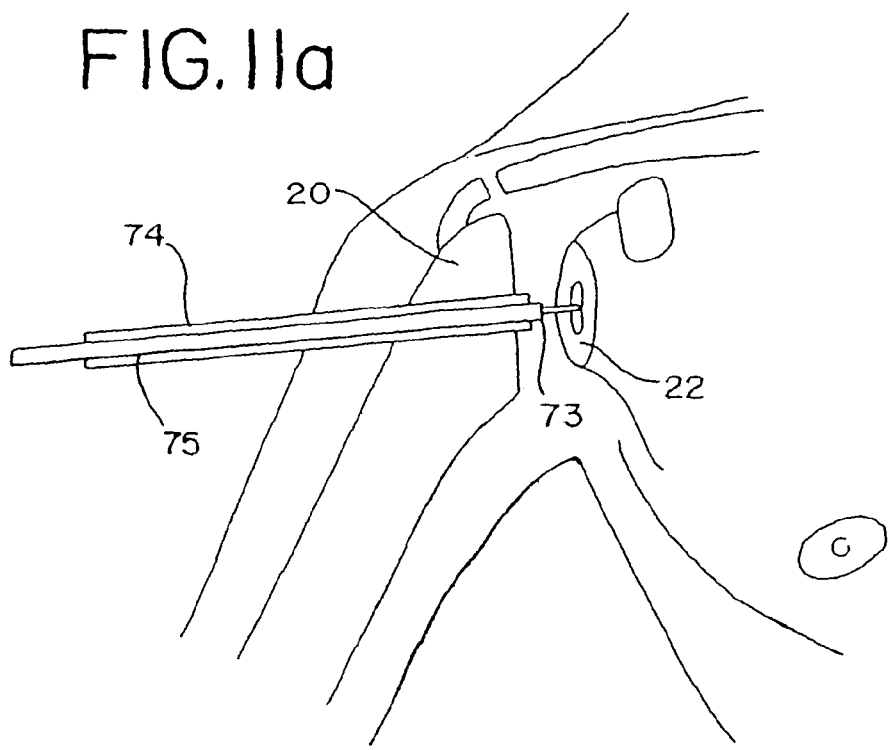
FIG. 11a is a schematic of a way of preparing a glenoid to accept a conventional keel glenoid implant with a transhumeral burr for a conventional proximal humeral implant during an embodiment of a surgical technique in accordance with the present invention.
Figure 11B:
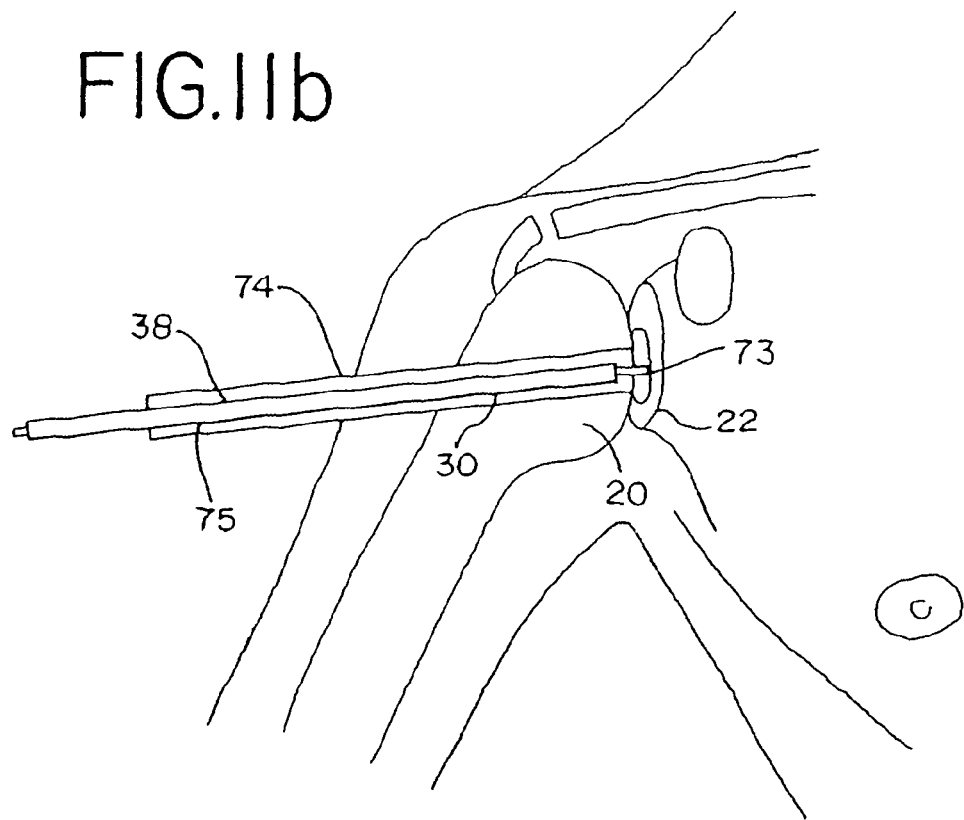
FIG. 11b is a schematic of a way of preparing a glenoid to accept a conventional keel glenoid implant with a transhumeral burr for a novel proximal humeral implant during an embodiment of a surgical technique in accordance with the present invention.

To further prepare the glenoid surface for a conventional glenoid implant, the humerus is positioned and translated such that the transhumeral keel/glenoid drill 66 is maintained perpendicular to the glenoid peg/keel guide surface 69. With the gleonid drill introduced through the transhumeral protective sheath 38 of the transumeral portal 30 and the glenoid drill guide 68 postioned from the first anterosuperior passage, holes are drilled into the glenoid (FIGS. 10*a-c*). To prepare the glenoid to accept a keel glenoid implant, the transhumeral burr 74 is inserted into the transhumeral portal 30 through the transhumeral protective sheath 38 and used to connect the drilled holes in the glenoid 22 surface (FIGS. 11*a-b*).

In one embodiment, the transhumeral burr 74 has a transhumeral shaft 75 removably attached to a high speed burr tip 73 with different sizes used for cutting holes in a glenoid 22, particularly for a keel.

Figure 12A:
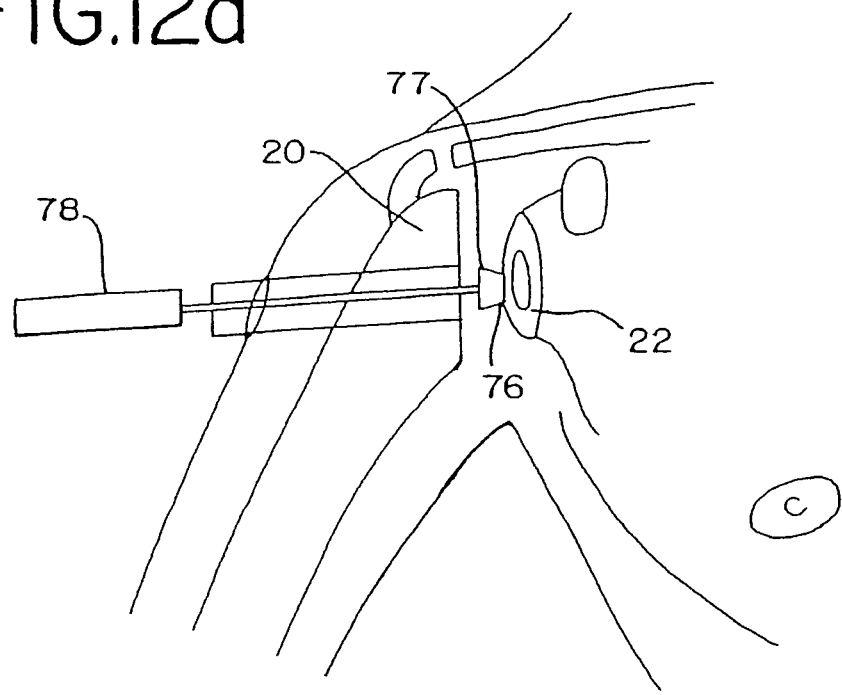
FIG. 12a is a schematic of a way of preparing a glenoid to accept a conventional keel glenoid implant with a transhumeral keel punch for a conventional proximal humeral implant to be used in an embodiment of a surgical procedure in accordance with the present invention.
Figure 12B:
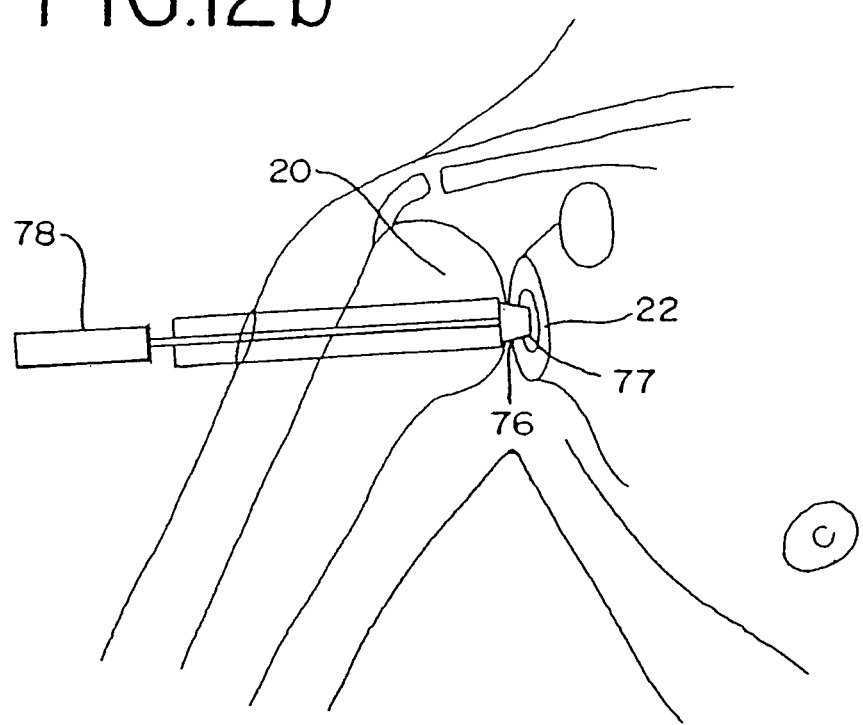
FIG. 12b is a schematic of a way of preparing a glenoid to accept a conventional keel glenoid implant with a transhumeral keel punch for a novel proximal humeral implant to be used in an embodiment of a surgical technique in accordance with the present invention.
Figure 13E:
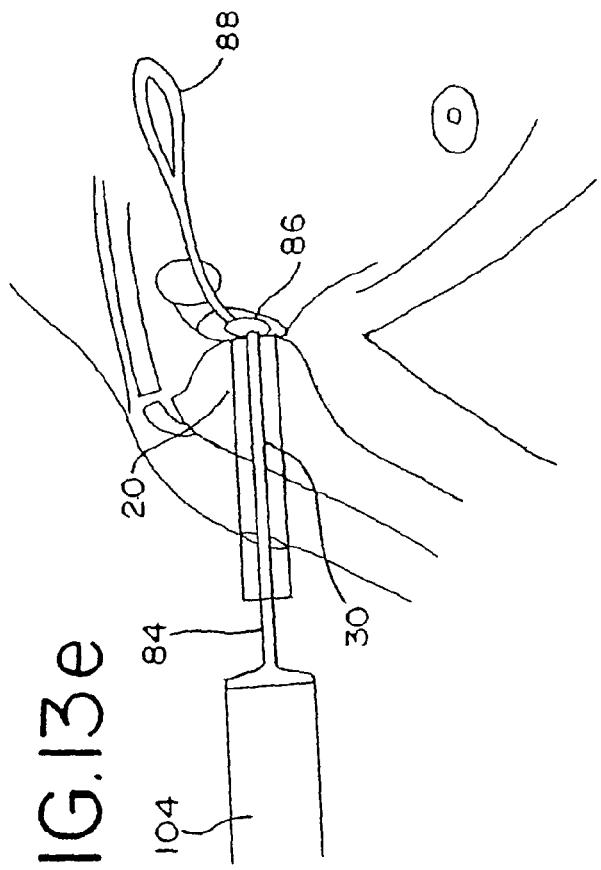
FIG. 13e is a schematic of a way of utilizing an embodiment of a transhumeral cementation catheter and glenoid cement pressurizer for a novel proximal humeral implant to be used during a surgical procedure in accordance with the present invention.
Figure 13A:
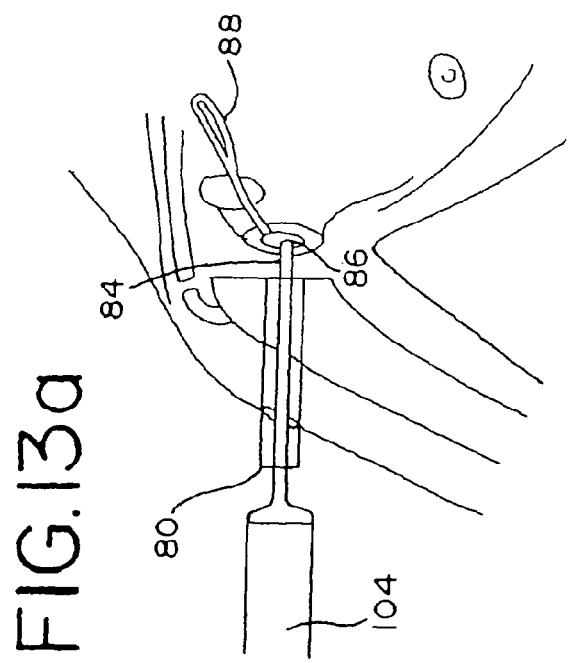
FIG. 13a is a schematic a way of utilizing an embodiment of a transhumeral cementation catheter and glenoid cement pressurizer for a conventional proximal humeral implant to be used during a surgical procedure in accordance with the present invention.
Figure 13D:
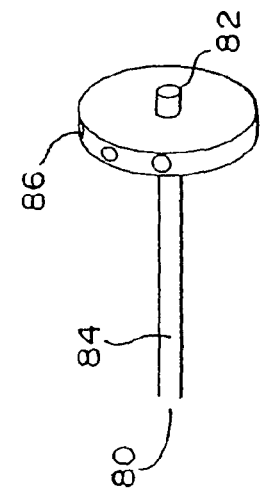
FIG. 13d is an exploded view of an embodiment of a glenoid cement pressurizer tip for a peg implant of FIGS. 13a and c, in accordance with the present invention.
Figure 13C:
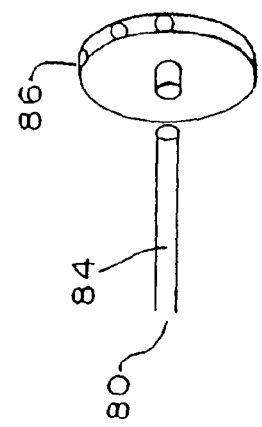
FIG. 13c is an exploded view of an embodiment of a glenoid cement pressurizer tip of FIGS. 13a and b in accordance with the present invention.
Figure 13B:
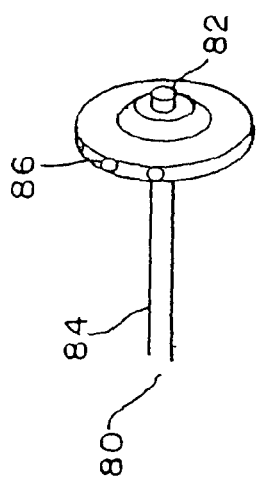
Figure 14A:
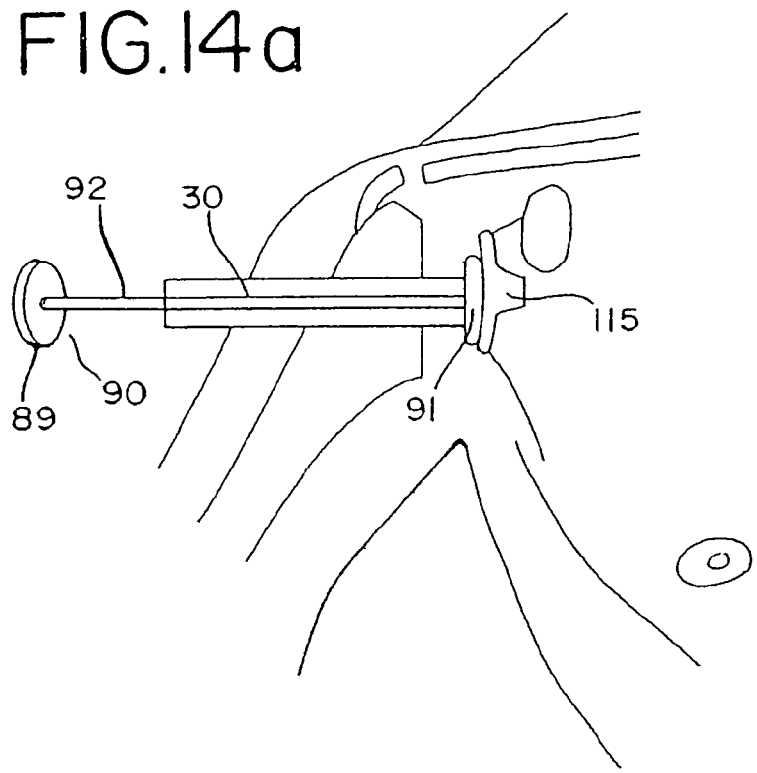
FIG. 14a a schematic of a way of utilizing an embodiment of a transhumeral glenoid impactor for a conventional humeral implant during a surgical procedure of the present invention.
Figure 14B:
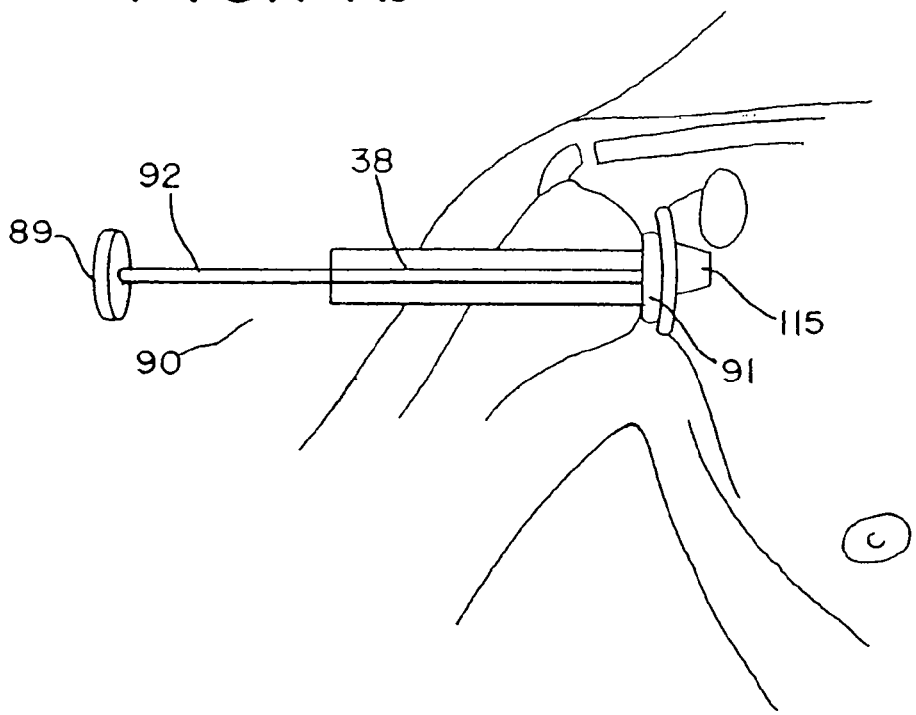
FIG. 14b is a schematic of a way of utilizing an embodiment of a transhumeral glenoid impactor for a novel humeral implant during a surgical procedure of the present invention.

A modular keel punch 76 is used to finish the glenoid keel cut. In an embodiment, where a glenoid keel punch 76 is used, the keel punch 76 has a working surface 77 and a removably attached transhumeral shaft 78 (FIGS. 12*a-b*). The working surface 77 (also referred to as a punch head,) is inserted through the first anterosuperior passage and the shaft 78 is introduced through the second anterosuperior passage and the transhumeral protective sheath 38. The shaft 78 is assembled with the working surface 77 in the glenohumeral joint. The working surface 77 is a head shaped like a keel with cutting teeth to cut a keel shape into a glenoid surface 22. The punch 76 is struck with a hammer to complete the keel shaped cut into the glenoid (FIGS. 12*a-b*).

The humeral head and glenoid trial implants are inserted through the anterosuperior passage and the rotator interval retractor 5 (FIG. 2) is temporarily removed. There are different humeral trial implants that can be used, one for the conventional implant and one for a novel implant. In either case, both can mate with trial modular stems through the transhumeral portal. If there is not sufficient bone available to stabilize the conventional humeral trial with a transhumeral trial stem or the humeral surface is too far offset from the intramedullary axis of the humeral shaft to accurately trial, the intramedullary canal of the humerus can be prepared and fitted with a conventional intramedullary stem trial using conventional techniques and instruments from the anterosuperior passage. Because the rotator cuff has not been transected, it is much simpler to determine the proper size implant required to restore the normal musculotendinous length and tension in the rotator cuff and thus, more accurately restore the native anatomical dimensions of the joint. Fluoroscopy can also be used to judge proper implant size.

Next, the glenoid 22 is prepared to affix its conventional implant 115 using transhumeral cementation tools 80 (FIGS. 13*a-e*). A transhumeral irrigation and suction catheter is inserted into the transhumeral portal 30 through the novel transhumeral protective sheath 38 and used to irrigate and suck the prepared glenoid 22 holes dry. A transhumeral irrigation and suction catheter is used in yet another embodiment of the present invention. The irrigation and suction catheter includes semi-rigid tubing that is inserted through the second anterosuperior passage and the transhumeral protective sheath 38 in the transhumeral portal 30 in order to irrigate or suction the prepared glenoid surface. The catheter attaches to both, a fluid pump and suction tubing, and may be easily switched between the two with a stopcock-like device.

The peg or keel holes are temporarily packed with thrombin soaked gel pads or epinephrine soaked gauze using a novel transhumeral forceps device. The transhumeral irrigation and suction catheter is used again to clean and dry the holes and a transhumeral cementation catheter 84 is inserted through the transhumeral portal 30 and protective sheath 38 to place the cement.

Note that the above-described transhumeral cementation tool 80 includes a keel glenoid or peg glenoid cement pressurizer head 86 and a cementation catheter 84. The transhumeral cementation catheter 84 includes semi-rigid tubing which connects to a conventional cement gun 104 to deliver cement to the site of implant fixation to bone. The head 86 includes a keel glenoid or peg glenoid cement pressurizer tip 82 that is cannulated and fits into a respective keel or peg-shaped prepared hole in the glenoid surface to dispense cementation material under pressure into that hole in the glenoid surface 22. The pressurizer heads 86 are shaped similar to a glenoid implant with a smaller keel or single peg. The radius of curvature of the periphery of the tip 82 matches that of the reamed bony glenoid surface 22 to help seal the hole during cement insertion. These heads 86 are inserted through the first anterosuperior passage by their handles 88 and are attached to the transhumeral cementation catheter 84 within the glenohumeral joint 9 to pressurize the cement in the glenoid 22 holes. The handle 88 is removable and can be attached to the head 86 at different positions to allow it to be inserted from variable angles through the anterosuperior passage. The cementation head 86 limits the escape of cementation material from the hole and allows pressure to build up which forces the cement deep into the interstices of the trabecular bone to allow improved fixation. A cement pressurizer tip 82 may be inserted into the joint through the anterosuperior passage and assembled with the transhumeral cementation catheter 84. There are different pressurizer tips 82 to match either the pegged or keeled glenoid. The conventional glenoid implant 115 is inserted through the anterosuperior passage, is seated and held in place until the cement dries with a modular transhumeral glenoid impactor 90. Excess cement is removed and the joint is irrigated The transhumeral glenoid impactor 90 includes a transhumeral shaft 92 which removably attaches to a working head 91. The working head 91 has a convex surface that approximates the radius of curvature of the articular surface of the glenoid implant. The shaft 92 is introduced through transhumeral protective sheath 38 within the transhumeral portal 30. The working head 91 is introduced through the first anterosuperior passage and mated with the transhumeral shaft 92. Force can then be applied to the handle 89 of the impactor 90 to seat the glenoid implant 115.

In accordance with an embodiment of the present invention, a multiple peg glenoid implant 117 (FIGS. 20a-c) or a novel modular ingrowth glenoid implant 118 (FIGS. 26a-b, 27a-c) can also be inserted.

Figure 20A:
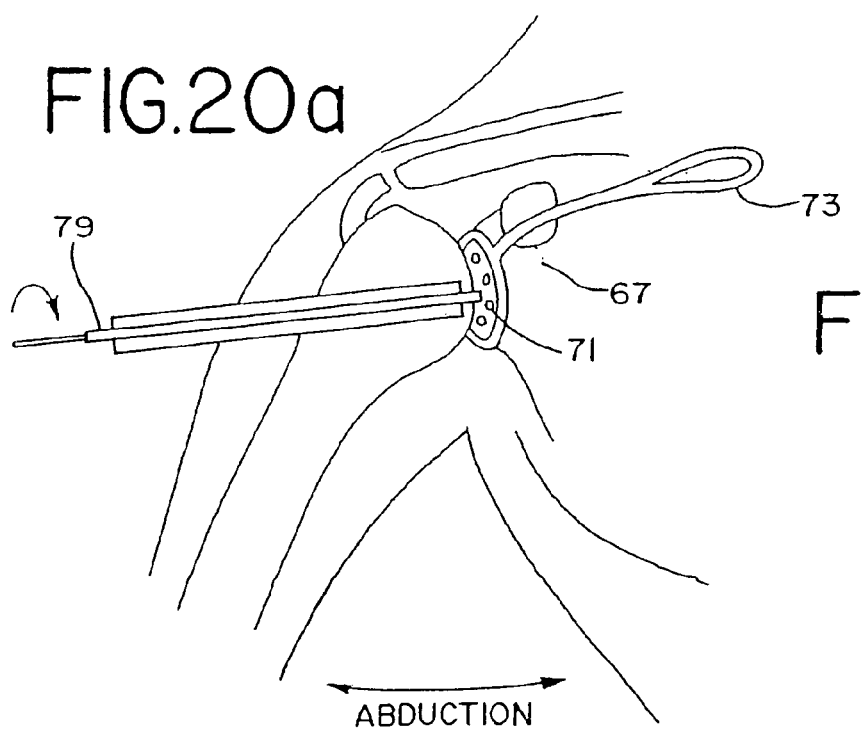
FIG. 20a is a schematic a way of inserting a multiple peg glenoid surface to be used in an embodiment of a surgical technique in accordance with the present invention.
Figure 20C:
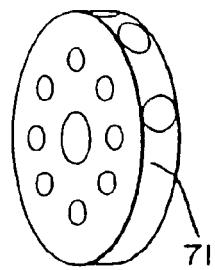
FIG. 20c is a perspective view of a multiple peg glenoid guide of FIG. 20a in accordance with the present invention.
Figure 21:
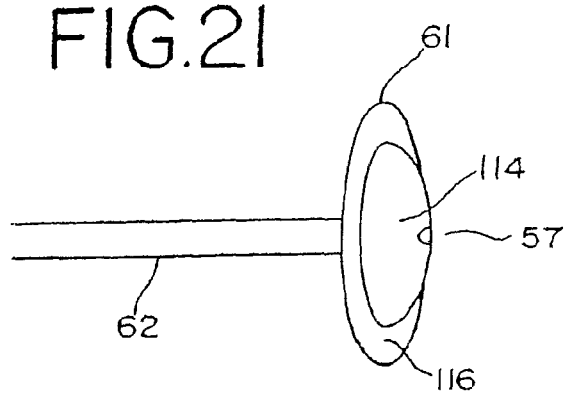
FIG. 21 is a side perspective view of an embodiment of a novel transhumeral glenoid reamer in accordance with the present invention.
Figure 22:
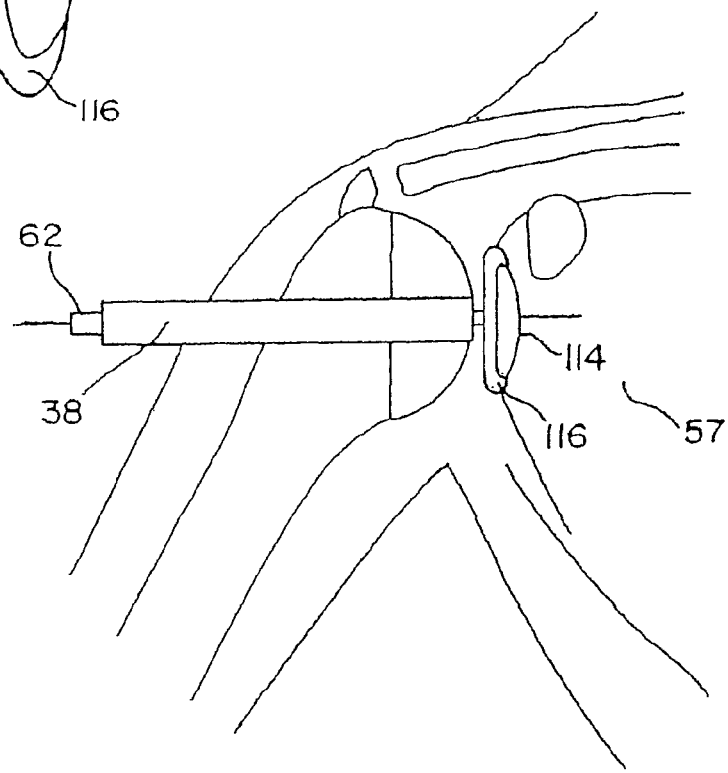
FIG. 22 is a schematic of a way of utilizing a novel glenoid reamer in an embodiment of a surgical technique in accordance with the present invention.

After the glenoid surface 22 has been reamed by a glenoid reamer 58 as described previously, the multiple glenoid pegs 17 can be introduced with a novel multiple peg guide 72 through the anterosuperior passage and inserted into the prepared surface of the glenoid 22 using a transhumeral insertor device 79 (FIG. 20a). In another embodiment, a multiple peg glenoid insertor 79 and insertor guide 72 are used. The multiple peg glenoid insertor guide 72 includes a handle 73 and a guiding surface 71. The guiding surface 71 is sized and shaped as the glenoid peg drill guide surface 69 discussed above. The guide 72 is introduced via the first anterosuperior passage and holds multiple pegs 117 to be inserted into the glenoid 22. The guiding surface 71 of the guide 72 controls the depth and location of insertion of the multiple pegs 117.

The multiple peg glenoid insertor 79 is inserted via the second anterosuperior passage and through the transhumeral protective sheath 38 in the transhumeral portal 30. It is used to engage the pegs 117 located within the multiple peg insertor guide working surface 71 and then drives them into the glenoid 22 one at a time. The insertor 79 stops when it hits the guide surface 71 to control the depth of peg 117 insertion. Drilling pilot holes through a separate guide with a special transhumeral drill can precede this step. The guide surface 71, preloaded with the implant pegs 117 controls the position, direction and depth of peg 117 insertion. The guide surface 71 has a protruding centering peg which fits into the centering hole of the glenoid to help center and position the guide surface 71.

After the multiple peg prosthesis is implanted, trialing of a conventional or novel humeral implant can be performed as described previously.

Alternatively, a novel ingrowth glenoid implant 118 can be implanted after reaming the glenoid with a novel transhumeral glenoid reamer 57 as described previously. The novel modular ingrowth glenoid implant 118 has an ingrowth shell 120 and modular wear-resistant articulating surface 122 (FIGS. 23a-b, 26a-b, 27a-c)

The ingrowth shell 120 of the glenoid implant 118 is a cannulated shallow shell with a protruding surface 119 that sits within the concavity of the reamed glenoid surface. The protruding surface is surrounded by a flat outer surface 121 (or brim). The protruding surface 119 may be any shape such as a square, pyramidal, hemispheric, triangular or any other suitable shape. The protruding surface 119 protrudes into the glenoid 22 to a specified depth. The depth is such that it is enough for the ingrowth shell 120 to be securely seated within the glenoid 22 and for the wear-resistant surface 122 to fit therein (as described below) and yet not so deep that a large amount of subchondral bone must be reamed from the glenoid 22. Preferably, the shape of the previously described novel glenoid reamer 57 is the same as the shape of the protruding surface 119 of the ingrowth shell 120 such that there will be a secure fit when the ingrowth shell 120 is seated within the glenoid 22. As the ingrowth shell 120 is pressed into the glenoid, the flat surface (or annular brim) 121 of the ingrowth shell 120 also makes contact with the peripheral glenoid surface 22, and in fact, provides a stopping point of insertion. The ingrowth shell 120 is made of suitable material, examples of which include, but are not limited to metal, tantalum, porous metal, trabecular metal, ceramic materials, and titanium. The protruding surface 119 and the annular brim 121 of the shell 120 may also maintain a surface of a bony ingrowth material, as described in connection with the humeral implant below. This ingrowth material promotes bone growth and adhesion of the shell to the glenoid surface. The ingrowth shell 120 has a thickness of 0.1 to 10 mm, preferably from 0.1 to 2 mm. The ingrowth shell 120 has holes for fixation. These holes may be central 124 and peripheral 126 and may further be smooth, threaded or a combination thereof. In one embodiment, a shell has a central hole 124 and multiple peripheral holes 126, for example three peripheral holes 126. The central hole 124 is preferably smooth and the peripheral holes 126 are preferably threaded.

After reaming, the ingrowth shell 120 is inserted through the anterosuperior passage and impacted into the concavity (which matches the shape of the reamer head 61 and that of the protruding surface 119 of the ingrowth shell 120 to be implanted,) of the reamed glenoid with a transhumeral impacting device 90. The concavity is slightly undersized to attain a tight fit upon impaction. The ingrowth glenoid shell 120 is then fixed to the glenoid 22 using screws 133, 135. In one embodiment, a central compression screw 133 is first used to compress the ingrowth shell into the concavity created in the glenoid and affix the ingrowth shell 120 to the glenoid and then fixed angle peripheral screws 135 are used to lock the ingrowth shell into place (FIGS. 25a-b, 26a-b).

Figure 24A:
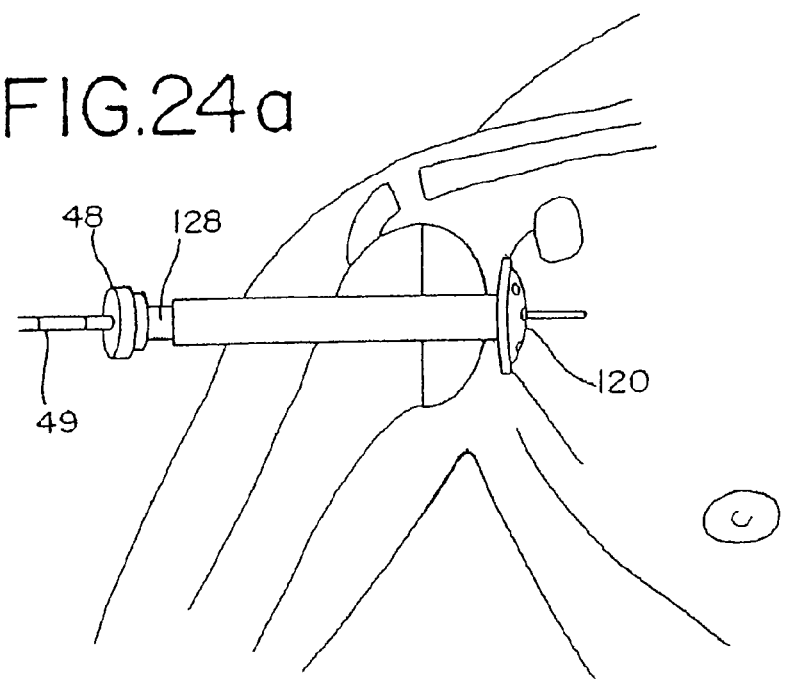
FIG. 24a is a schematic of a way of drilling screw holes into a glenoid utilizing a glenoid drill guide sleeve and glenoid screw guide sleeve in an embodiment of a surgical technique of the present invention.
Figure 24B:
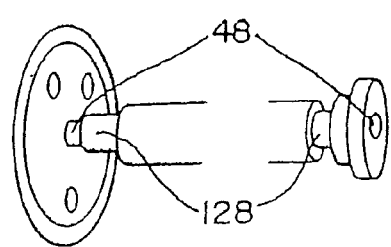
Figure 25A:
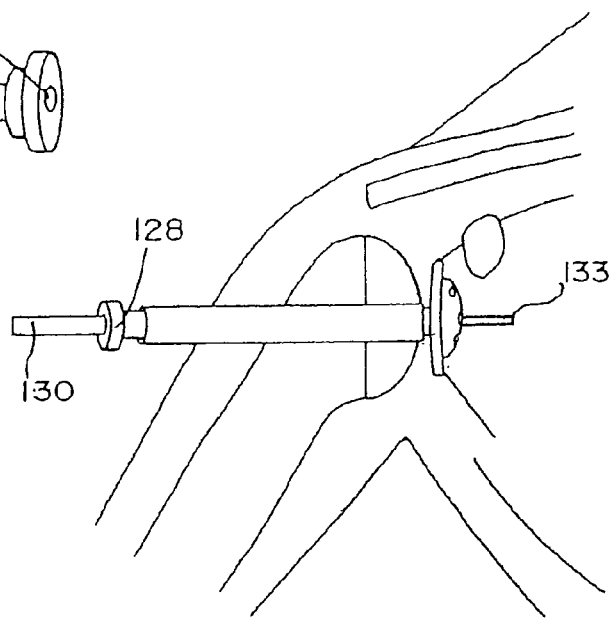
FIG. 25a is a schematic of a way of utilizing a glenoid screw guide sleeve and transhumeral screwdriver in accordance with an embodiment of a surgical technique of the present invention.
Figure 25B:
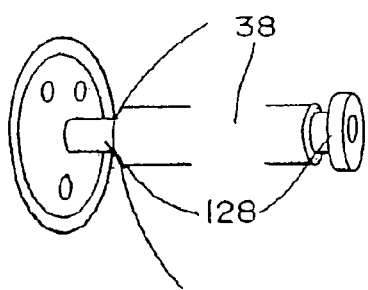
Figure 26A:
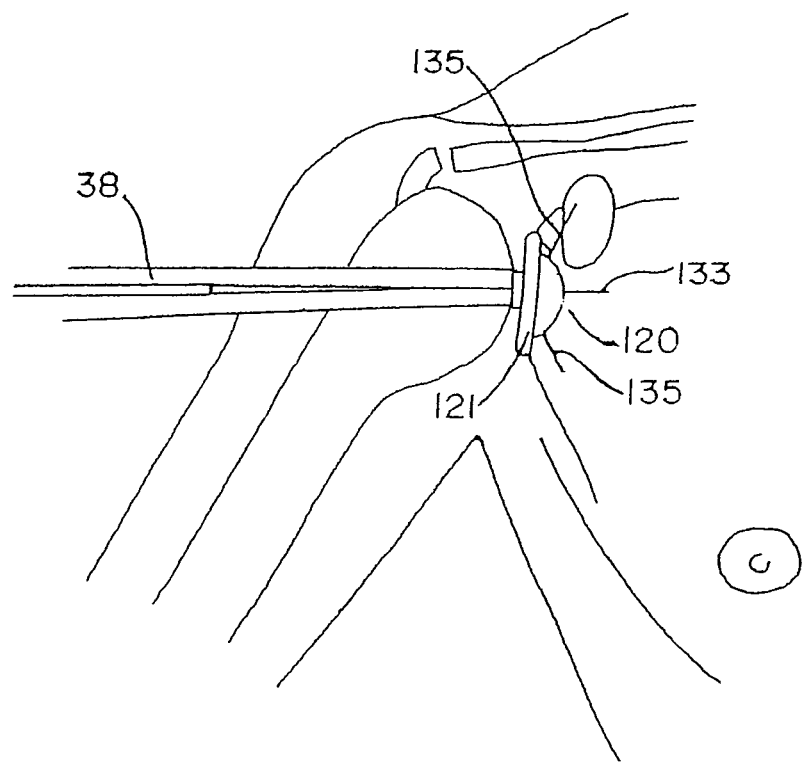
FIG. 26a is a schematic of utilizing a transhumeral impactor to secure a novel wear-resistant glenoid surface into an ingrowth shell of the novel glenoid implant in accordance with an embodiment of the present invention.
Figure 26B:
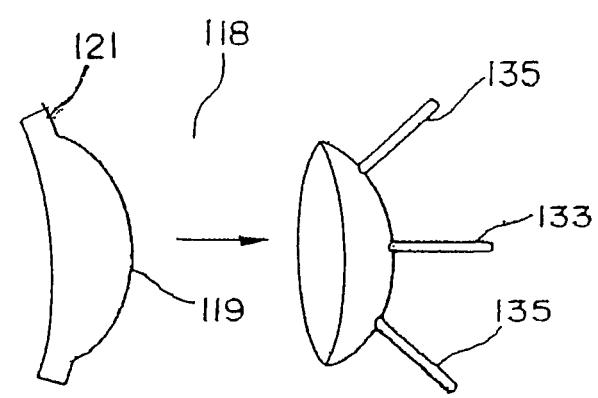
Figure 27A:
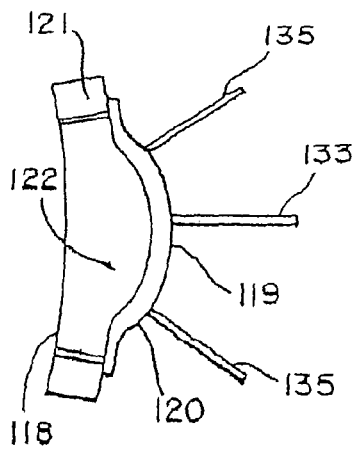
FIG. 27a is a side view of an embodiment of a novel glenoid implant in accordance with the present invention.
Figure 27B:
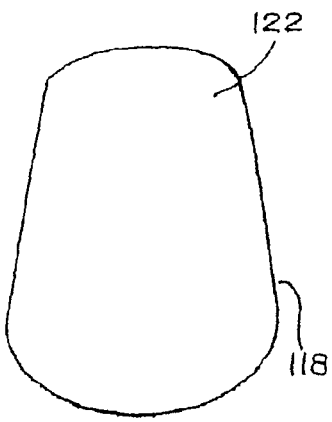
Figure 27C:
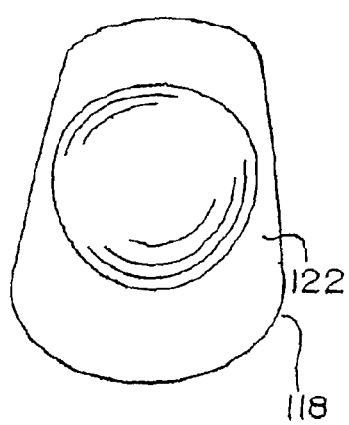
FIG. 27c is a bottom plan view of an embodiment of the novel wear-resistant surface of novel glenoid implant of FIGS. 27a and b.

The transhumeral glenoid drill 49 is used along with a transhumeral glenoid drill sleeve 48 (FIGS. 24a-b) to make the holes for the glenoid screws 133, 135. The transhumeral glenoid drill sleeve 48 fits into a transhumeral glenoid screw sleeve 128 which fits into the protective transhumeral sheath 38 in the transhumeral portal 30. The drill sleeve 48 mates with the holes 124, 126 in the ingrowth shell component 120 of the novel glenoid implant 118 to direct the drill 49 in the proper orientation. The shaft of the transhumeral glenoid drill 49 just fits within the inner diameter of the transhumeral glenoid drill sleeve 48 and has visible markings on it that allow one to measure the depth of the hole off the distant edge of the transhumeral drill sleeve 48 (FIGS. 24a-b). The drill 49 is advanced until the far cortex of the glenoid and scapula is reached. At which point, the surgeon reads the mark on the drill at the level of the glenoid drill guide sleeve 48. Approximately 5 mm is added to the screw length to determine the length of screw used. The drill 49 is then advanced through the far cortex to complete the screw hole in the glenoid 22.

In one embodiment of the present invention, a novel transhumeral screw driver 130 and transhumeral glenoid screw guide sleeve 128 are used to place the above described screws 133, 135. After drilling, the surgeon removes the inner transhumeral glenoid drill guide sleeve 48 and the transhumeral screwdriver 130 is inserted through the previously positioned transhumeral glenoid screw guide sleeve 48. The screw driver shaft 130 fits snuggly within a transhumeral glenoid screwdriver guide sleeve 128. The screwdriver 130 is then advanced to place a screw 133, 135 through a hole 124 or 126 of the ingrowth shell 120 of a novel glenoid implant 118 into the drilled glenoid bone 22. As briefly described above, a central screw 133 is first inserted through a central smooth hole 124 in the glenoid shell 120 to initially compress the ingrowth shell 120 firmly into the glenoid surface 22. The glenoid ingrowth shell 120 is then locked into place by at least one peripheral screw 135, preferably three (FIGS. 25a-b, 26a-b). For example, if three peripheral screws 135 are utilized, one is placed anterosuperiorly, one is placed posterosuperiorly, and one is placed inferiorly. The threads of the screws 135 engage the threading of the peripheral holes 126 in the glenoid ingrowth shell 120 as well as the drilled outer cortical surface of the glenoid 22 and scapula. The peripheral holes 126 of the shell 120 direct the screws 135 into a fixed divergent pattern.

After the glenoid ingrowth shell 120 is well fixed, the modular wear-resistant glenoid surface 122 is inserted though the anterosuperior passage and impacted into the shell 120 with a transhumeral glenoid impactor 90 (FIGS. 14a-b, 26a-b) as described previously.

The wear-resistant surface 122 of the glenoid implant 118 has a convex surface which mates with the concave side of the protruding surface 119 of the ingrowth shell 120 and forms the articulating surface of the glenoid implant 118. The protruding surface 119 of the ingrowth shell 120 is of thin dimension such that it simultaneously provides 1) fixation to the glenoid bone; 2) an ingrowth surface; 3) provides a support surface for the wear-resistant surface 122; and 4) a recessed coupling device which maximizes the thickness of the wear-resistant surface 122 for durability and while still maintaining proper anatomic glenohumeral surface relationships. The wear-resistant surface 122 may include, but is not limited to polyethylene, plastic, ceramic material, metals, and magnetic materials. At a minimum, the wear-resistant surface 122 has a thickness of 0.1 to 15 mm, preferably 4 to 7 mm, if composed of currently available forms of polyethylene, protruding above the glenoid bony surface and flat outer surface (or annular brim) 121 of the ingrowth shell 120. It may have variable thickness along its dimension to correct version of glenoid. The wear-resistant surface 122 of the glenoid implant 118, which is approximately pear shaped, has both a superior-inferior dimension and an anterior-posterior dimension. The superior-inferior axis has a suitable range of from about 20 to 60 mm, preferably from about 30 to 48 mm. The anterior-posterior axis defines an upper half and a lower half. The lower half anterior-posterior axis has a range of about 15 to 50 mm, preferably from about 21 to 35 mm. The upper half has a range of from about 10 to 50, preferably 18 to 33 mm. The ratio of the upper half to the lower half is approximately 0.8 to 1.0. The ratio of the lower half of the anterior-posterior axis to the superior-inferior axis is approximately 0.7 to 1.0, whereas the ratio of the upper half of the anterior-posterior axis to the superior-inferior axis is approximately 0.6 to 1.0. In addition, the radius of curvature of the superior-inferior axis of the glenoid surface is greater than the coronal radius of curvature of the humeral surface of the humeral implant with which the glenoid implant articulates. The anterior-posterior radius of curvature of the glenoid surface is larger than the axial radius of curvature of the humeral surface. It may have variable thickness along its dimension to correct version of glenoid.

To prepare the humerus for a conventional humeral implant, the humerus is adducted and extended to line up the axis of the intramedullary canal with the first anterosuperior passage. With the self-retaining rotatory interval retractor 5 in place, the humeral canal is prepared using conventional instruments, trials are used to determine the proper fit and size of the implants, and the proper conventional humeral implant with an intramedullary stem is either cemented or press-fit into the proximal humerus 20 in accordance with the present.

For the novel humeral implant 94, the humerus does not require special positioning. After humeral trialing, the novel humeral stem 98 is placed in the transhumeral portal 30 from either the first or second anterosuperior passages and the novel modular head 96 is inserted through the anterosuperior passage. The two components 96, 98 are then mated together.

Figure 15A:
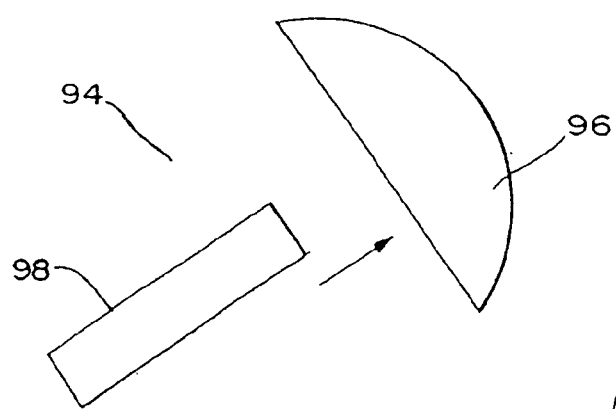
FIG. 15a is a exploded view of humeral implant in accordance with the present invention.
Figure 15B:
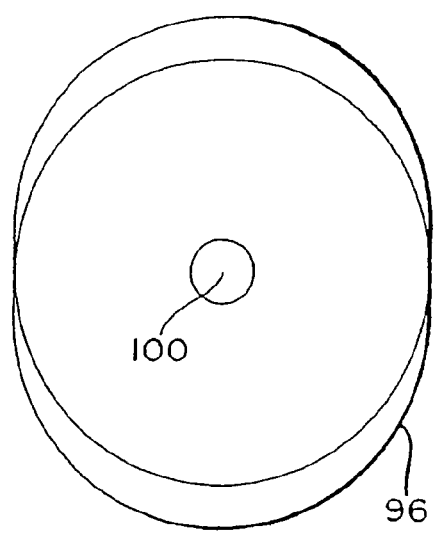
FIG. 15b is a bottom plan view of a humeral implant in accordance with the present invention.

The novel humeral implant 94 in accordance with the present invention is modular and includes a humeral surface 96 component, a roughly hemispheric shaped surface with a short central mating device 100, and a transhumeral stem 98 which fills the transhumeral portal 30 (FIGS. 15a-b). Alternatively, a novel humeral surface implant that includes only a humeral surface 96, with no stem 98 may be used when warranted. Preferably, however, a novel humeral implant 94 with two components 96, 98 is used. The two components, the humeral surface 96 and stem 98, are removably attached to one another. The humeral surface 96 has a coronal radius of curvature and an axial radius of curvature. The humeral surface can be spherical in shape. Preferably the humeral surface can be more anatomic being spherical, with equal coronal and axial radii of curvature, in the center and elliptical, with larger coronal than axial radii of curvature, at the periphery. A suitable range for the coronal radius of curvature is from 10 to 50 mm, preferably from 19 to 28 mm, with approximately 81% of all men having a coronal radius of curvature ranging from 23-28 mm, and 79% of all women having coronal radius of curvature ranging from 19-22 mm. A suitable range for the axial radius of curvature of the humeral surface of the implant is from 10 to 50 mm, preferably from 18 to 26 mm. The humeral surface 96 of the implant 94 also has a depth and thickness. A suitable range for the depth of the humeral implant 94 is from 5 to 40 mm, preferably from 15 to 24 mm, and the depth is the same in both the coronal and axial planes. The humeral surface 96 thickness has a range of from 0.1 to 5 mm, preferably from 1 to 3 mm. The ratio of the depth to the coronal radius of curvature is approximately 0.7 to 0.9. See Table 1.

TABLE 1

| Radius of curvature (mm) | Depth (mm) | | |
|---|---|---|---|
| | 15-17 | 18-20 | 21-24 |
| 19-20 | 10 | 3 | 2 |
| 21-22 | 7 | 18 | 3 |
| 23-24 | 0 | 9 | 18 |
| 25-26 | 0 | 8 | 14 |
| 27-28 | 0 | 0 | 4 |

Table 1 shows suitable and preferred ranges of radius of curvature and depth for the humeral surface of the humeral implant. (See Iannotti J P, Gabriel J P, Schneck S L, et al. The normal glenohumeral relationships: an anatomical study of one hundred and forty shoulders. J Bone Joint Surg 1992; 74A(4): 491500.)

The humeral surface 96 of the humeral implant 94 may be spherically shaped or more of an elliptical shape which better approximates the anatomy of a natural humeral head. The humeral surface 96 may be made of a variety of materials including, but not limited to cobalt-chrome alloys, ceramic materials, metals, and magnetic materials. It is contemplated that the humeral surface may also have fins, spikes, or other protuberances on its concave, non-articular surface to enhance rotational stability. Additionally, the concave, non-articular surface may also contain a bony ingrowth material. A bony ingrowth material allows the bone to which the implant is attached to grow into the implant and aids in attaining long-lasting fixation of the implant. These ingrowth materials, include, but are not limited to autologous and allograft osteoprogenitor cells and tissues, bone-morphogenic proteins, hydroxyapaptite coating, trabecular metal, porous metal, porous metal coating, and tantalum. It is contemplated that the surface of the humeral surface component 96 of the implant 94 that articulates with the glenoid or the glenoid implant, is smooth with a low coefficient of friction.

The stem 98 of the modular humeral implant 94 is sized to fit within the transhumeral portal 30 located along the central axis of the neck of the humerus. By fitting, it is meant that the stem 98 fits in a tight manner and is stable in that location. As it is contemplated that the transhumeral portal 30 has a diameter of from 0.1 to 5 cm, the diameter of the stem 98 is also from 0.1 to 5 cm, and is dimensioned to fit within the transhumeral portal 30. The stem 98 may be composed of any suitable materials including, but not limited to titanium, stainless steel, cobalt-chrome alloy. The stem 98 may be smooth, textured, or threaded. Smooth glass bead blast finishes are another possibility. Threads may be uniform or may vary in width along the length of the stem. Further, the shape of the stem 98 is intended to accommodate the shape of the transhumeral portal 30, therefore it may be round, square, triangular, or any other geometric shape that may comprise the transhumeral portal 30. The main body of the stem 98 has a consistent cross-sectional shape and size along its straight longitudinal axis. Therefore, unlike conventional humeral implant stems, which are tapered and bowed to fit within the dimensions of the metaphysis and diaphysis of the humerus, the stem 98 of the present invention maintains a uniform diameter and is linear from end to end. As such, the stem is dimensioned to sit within the epiphyseal and metaphyseal portions of the humerus. As described for the humeral surface 96, the stem 98 may also contain fins or spikes to aid rotational stability, and it may also possess a bony ingrowth material surface, as describe above.

The stem 98 may be of varying lengths, a suitable range of which is from about 4 to 7 cm. The preferred length is dimensioned to extend from the lateral cortex of the humerus to the center of a humeral head. It is intended that this stem 98 be introduced into the transhumeral portal 30 via the second anterosuperior incision and advanced through the transhumeral portal 30 to a position that is suitable for mating with the humeral surface 96 which is inserted via the anterosuperior incision, described above. If appropriate, the stem 98 may also be inserted from the articular surface of the proximal humerus through the first anterosuperior passage.

The humeral surface 96 and stem 98 of the humeral implant 94 connect to one another via a mating site 100. The humeral surface 96 and stem 98 are joined within the glenohumeral joint space. They may be press fit, screwed together, or joined by morse taper, as well as any other suitable locking mechanism. It is possible for the male or female counterpart to be on either the stem 98 or the humeral surface 96, so long as one male counterpart and one female counterpart are present in the humeral implant 94.

Figure 16:
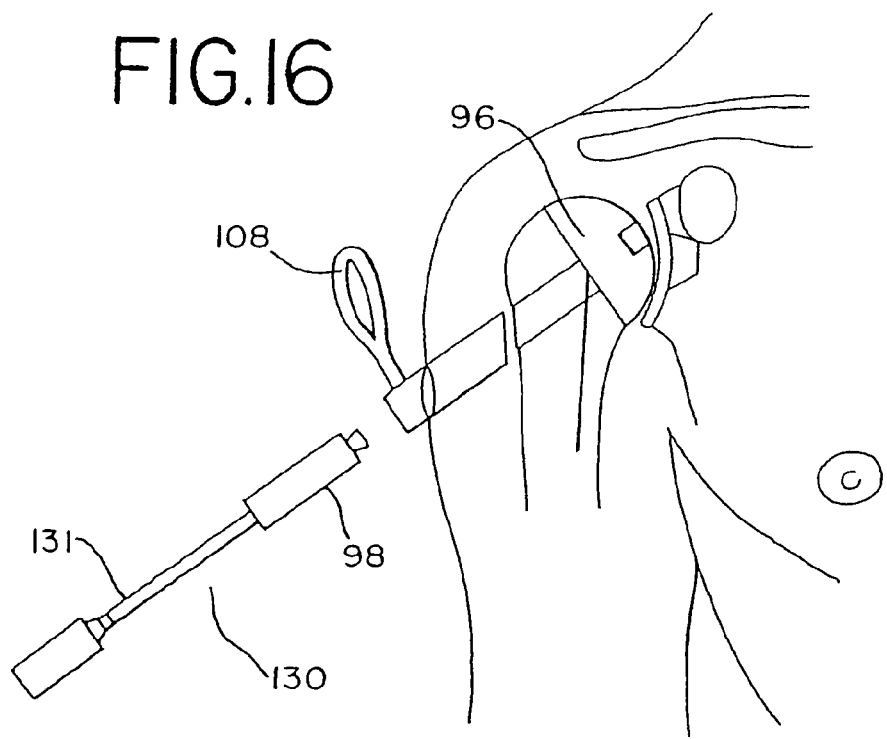
FIG. 16 is a schematic of an embodiment of a humeral surface implant, Example A, in accordance with the present invention.

The humeral surface 96 component is inserted through the anterosuperior passage and mated with its stem 98 placed through the transhumeral portal 30. The humeral surface 96 and modular stem 98 implant can be cemented or press-fit to the prepared humeral surface and there are many possible variations of the implant 94. Examples A, B, and C are various embodiments of a humeral implant 94 in accordance with the present invention. Example A includes a hemisphere shaped humeral surface 96 and a threaded transhumeral stem 98 (FIG. 16). The humeral surface 96 component is inserted through the anterosuperior passage and is either cemented or press-fit onto the humeral surface 20 and then impacted on the prepared humeral surface against the glenoid 22. The hemisphere shaped surface 96 is rotationally stabilized with a rod inserted into a hole at a peripheral edge of the hemisphere shaped surface 96 while the threaded humeral stem 98 is advanced through the protective sleeve 15 from the transhumeral portal guide 14 and up the transhumeral portal 30 to engage with the non-articular side of the hemisphere shaped humeral surface 96. The threaded stem 98 has a double pitch with finer pitched but deeper cancellous threads that engage and fill the transhumeral portal 30 and slightly wider pitched more shallow threads on the narrower diameter tip which engages the humeral surface 96 component so as to secure the humeral surface 96 component. Should it be necessary, removal of the example A implant 94 is conducted by recreating both anterosuperior passages, inserting a driver for the threaded stem 98 through the second anterosuperior passage, inserting a stabilizing rod into a peripheral edge of the humeral surface 96 component from the first anterosuperior passage and backing out the stem through the protective sleeve 15 from the transhumeral portal guide 14. The humeral surface 96 component is then removed by sawing across the base of the humeral surface 96 component at the anatomic neck of the humerus with a power or Gigli saw.

Figure 17A:
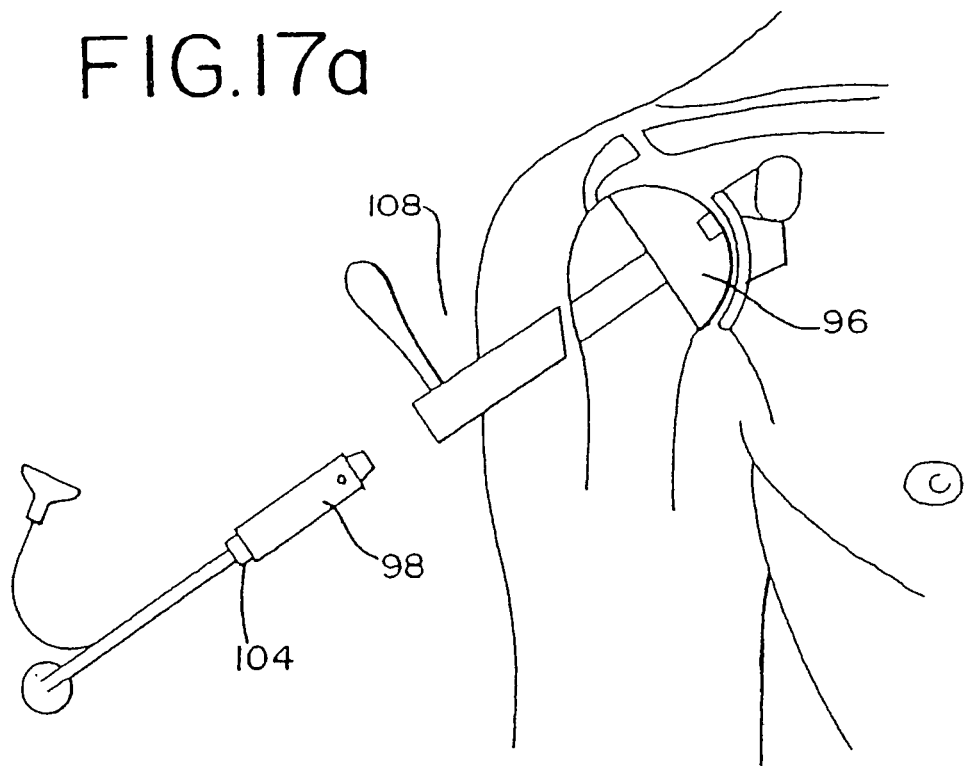
FIG. 17a is schematic of an embodiment of a humeral surface implant, Example B, in accordance with the present invention.
Figure 17B:
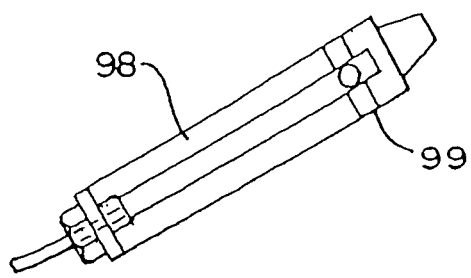
FIG. 17b is a perspective view of an embodiment of a stem with inner cement channels in accordance with the present invention.
Figure 17C:
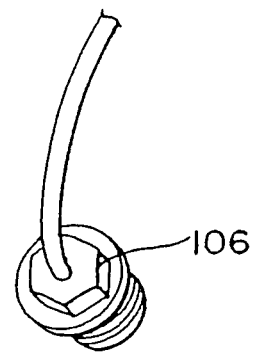
FIG. 17c is an perspective view of an embodiment of a endcap of the novel transhumeral stem of FIG. 17b in accordance with the present invention.
Figure 18A:
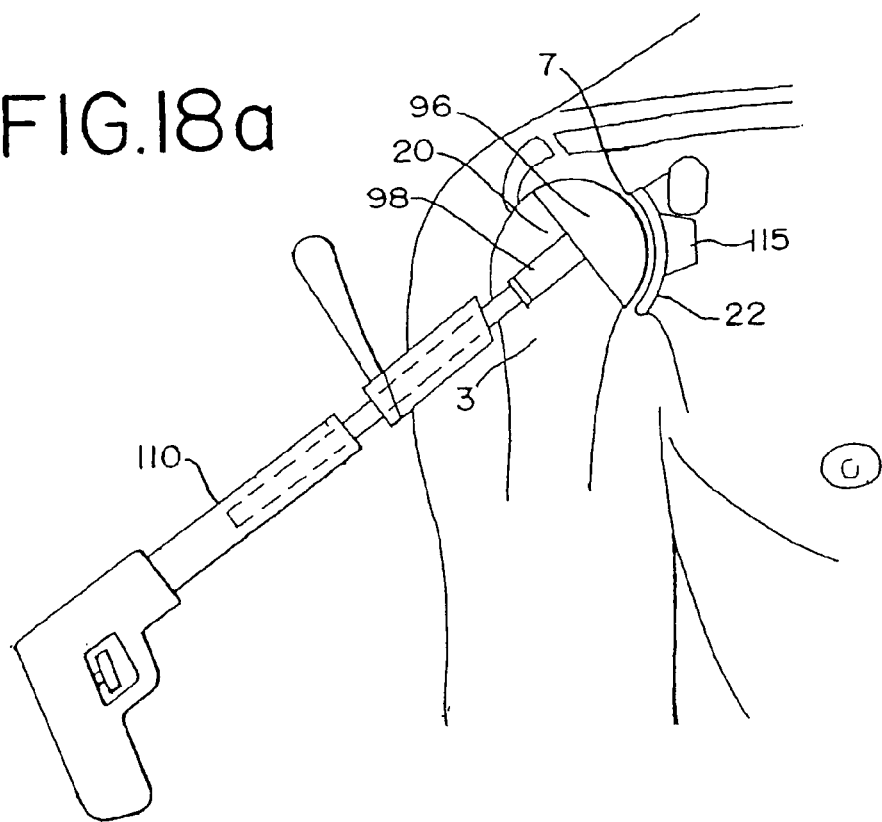
FIG. 18a is a schematic of a way of removing an embodiment of a humeral surface implant, Step 1, Example B, during an embodiment of a surgical procedure in accordance with the present invention.
Figure 18B:
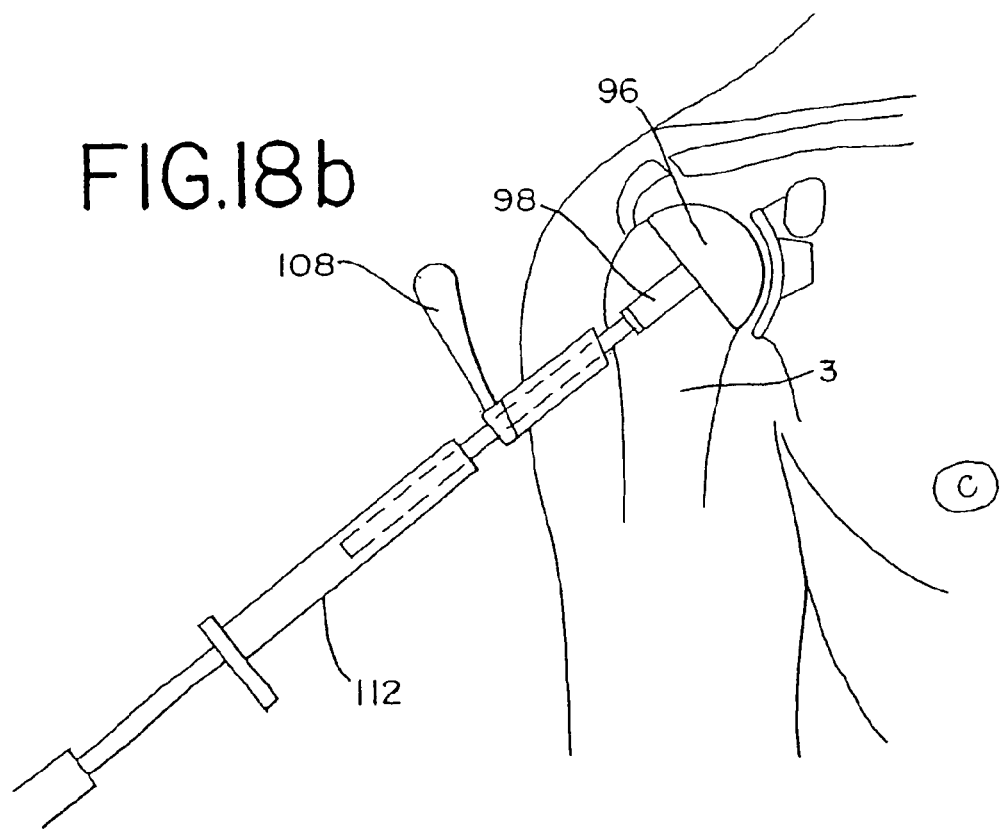
FIG. 18b is a schematic of a way of performing Step 2 of removing an embodiment of a humeral surface implant of FIG. 18a during an embodiment of a surgical procedure in accordance with the present invention.

Example B includes a similar humeral surface 96 component and a cemented transhumeral stem 98 (FIGS. 17*a-c*). Again, the humeral surface component 96 is inserted through the anterosuperior passage, is either cemented or press-fit onto the prepared humeral surface 20 and impacted on the prepared humeral surface 20 against the glenoid 22. Another transhumeral stem 98 which possesses the male end of a morse taper is inserted into the female end on the non-articular side of the humeral surface component 96 and impacted against the glenoid. This stem 98 may be press-fit or cemented to the bony transhumeral portal. An endcap 106 is threaded into the non-articular side of the stem 98 to assist with later removal of the humeral surface implant 94. To fix with cement, a cementation catheter 84 is assembled to an opening in the endcap 106 and cement is injected through the cannulated transhumeral stem 98 exiting holes 99 at its articular end. The cement is injected until it becomes visible around the non-articular end of the stem 98. Should it be necessary, removal of the example B implant is conducted by recreating the anterosuperior passages, removing the endcap with a T-handled wrench, threading the removal shaft 111 into the stem 98, drilling out the cement-implant interface with a coring reamer 110 over the stem 98, and disimpacting the stem 98 from the humeral surface component 96 with a disimpaction sleeve 112 (FIGS. 18*a-b*). The humeral surface component 96 is removed by sawing across the base of the humeral surface component 96 at the anatomic neck of the humerus with a power or Gigli saw.

Figure 19A:
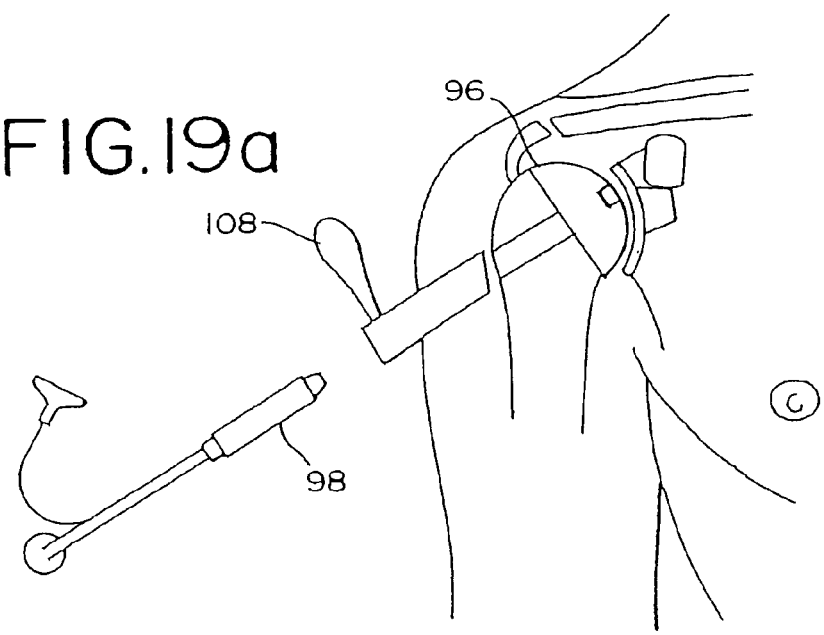
FIG. 19a is a schematic of inserting an embodiment of a humeral surface implant, Example C in accordance with the present invention.
Figure 19B:
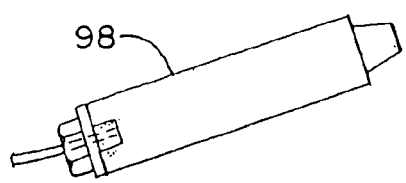
FIG. 19b is a perspective view of a stem of an embodiment of a humeral implant of FIG. 19a that is inflatable in accordance with the present invention.

Example C includes a similar humeral surface 96 component and an inflatable transhumeral stem 98 (FIGS. 19*a-b*) similar to technology used in the FIXION™ IM Nail (See "A New Expandable Implant for the Repair of Long Bone Fractures", Sinha, Anjoy M. D. et al, published in www.Healthfocus.com). Again, the humeral surface component 96 is inserted through the anterosuperior passage and either cemented or press-fit, and further impacted on the prepared humeral surface 20 against the glenoid 22. Another transhumeral stem 98 which possesses the male end of a morse taper is inserted into the female end on the non-articular side of the humeral surface 96 component and impacted against the glenoid 22. The inflatable stem 98 is an expandable tube that is reinforced with longitudinal bars and has a one-way valve system on the end that doesn't mate with the humeral surface component. Once positioned, the stem 98 is inflated or expanded from its collapsed position with a specialized saline pump to fill the stem 98, within the transhumeral portal 30, and gain purchase. The stem 98 can be removed by deflating it with the same pump and disimpacting the stem 98 from the humeral surface 96 component with a disimpaction sleeve 112. The humeral surface component 96 is removed by sawing across the base of the humeral surface 96 component at the anatomic neck of the humerus with a power or Gigli saw.

After the prosthetic implants, either humeral or glenoid, novel or conventional, are inserted as described above, the soft-tissue tension is evaluated, and the wounds are copiously irrigated, the deep passages, subcutaneous tissue, and skin are closed with sutures.

In yet another embodiment, the present invention is a glenohumeral joint with a transhumeral portal 30 along the central axis of the neck of the humerus and at least one implant. The implant may be a humeral implant 94, a glenoid implant 118 or both. The implants may be conventional implant or novel 94, 118 described herein.

In an alternative embodiment of the present invention, there is provided a method of repairing a rotator cuff, tear as shown in FIGS. 28-33. This procedure may be utilized in conjunction with the above described method of shoulder replacement or it may be used as a stand-alone procedure. In this method standard positioning and techniques for arthroscopic or open rotator cuff exposure are employed. If performed in conjunction with the previously described methods of shoulder replacement surgery, the anterosuperior passages may be used. If performed in isolation, an open deltoid split or arthroscopic subacromial exposure used for rotator cuff repair is performed in standard fashion. A small longitudinal stab is made through the skin and superficial deltoid fascia approximately 5-12 cm below the level of the anterolateral edge of the acromion.

Figure 28A:
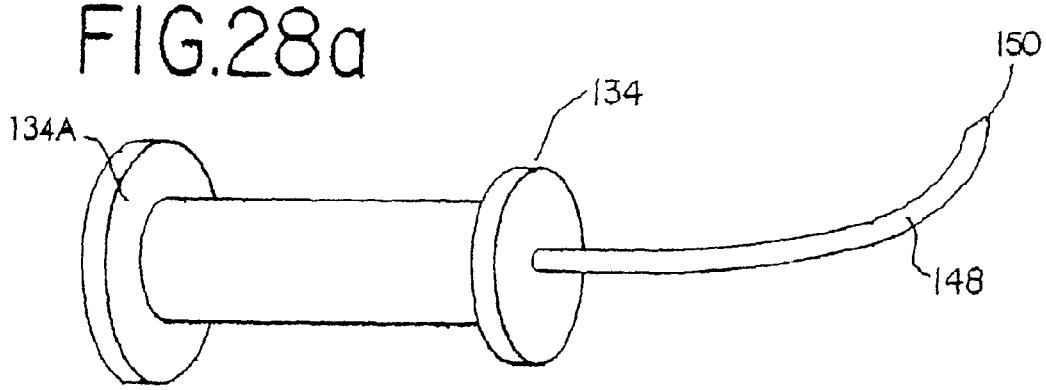
FIG. 28a is a perspective view of an embodiment of an insertional guide in accordance with the present invention.
Figure 28B:
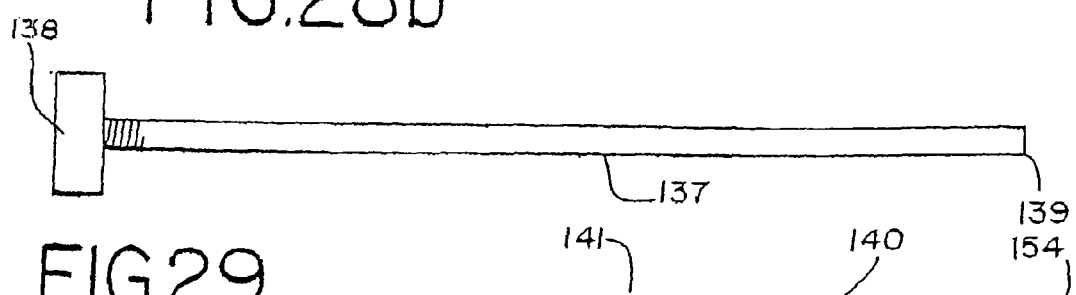
FIG. 28b is a perspective view of an embodiment of a flexible inner trocar of an embodiment of an insertion guide in accordance with the present invention.
Figure 29:
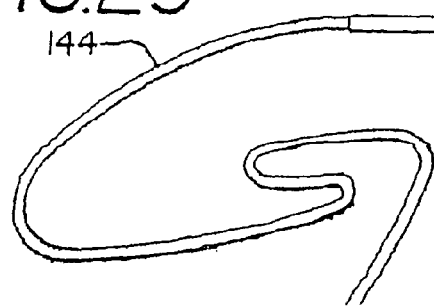
FIG. 29 is a perspective view of an embodiment of a suture pin of the present invention.
Figure 30:
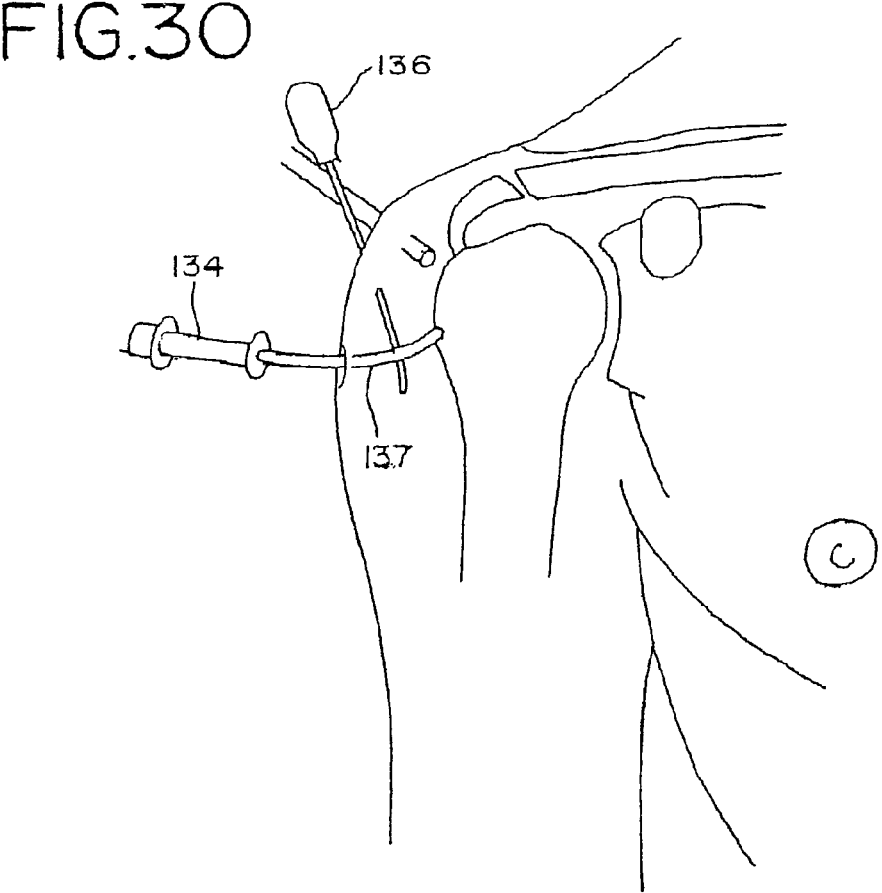
FIG. 30 is a schematic of a way of performing an embodiment of a surgical technique using the insertion guide of FIGS. 28-29 to bore into a greater tuberosity of proximal humerus in accordance with the present invention.
Figure 31:
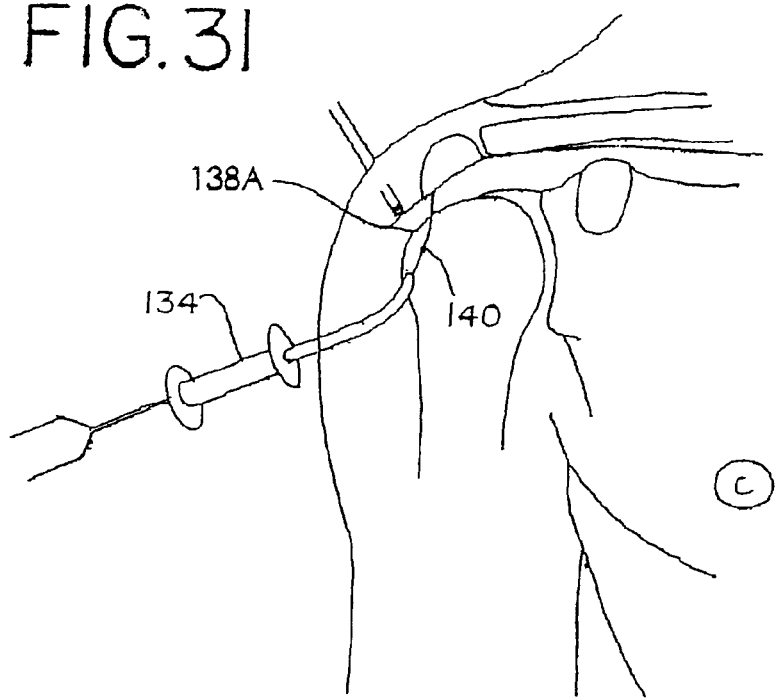
FIG. 31 is a schematic of a way of performing an embodiment of a surgical technique using the insertion guide of FIGS. 28-29 to advance the suture-pin device through the greater tuberosity of the proximal humerus and leading edge of rotator cuff tendon in accordance with the present invention.
Figure 32:
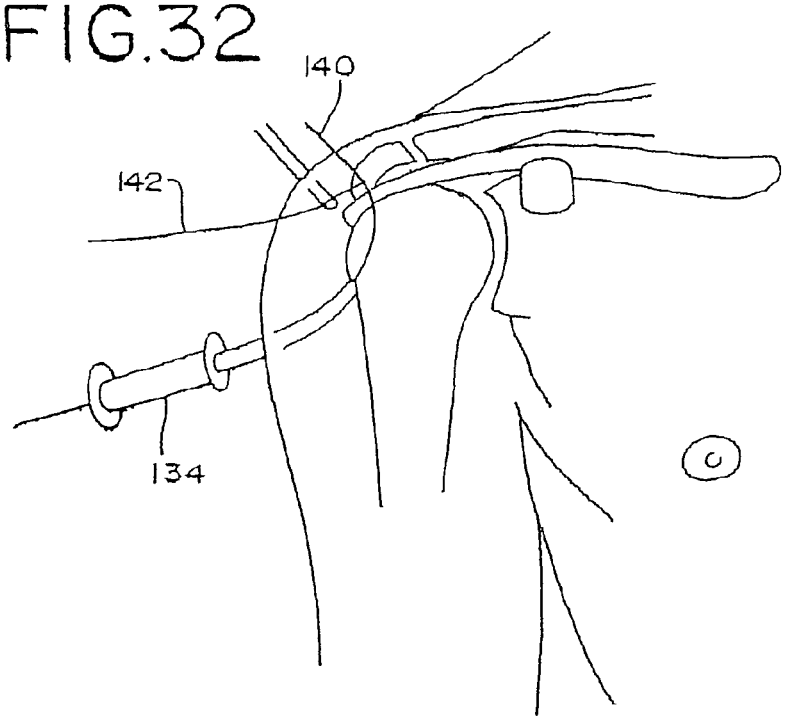
FIG. 32 is a schematic of a way of performing an embodiment of a surgical technique using a pin director to guide the pin out from the shoulder in accordance with the present invention
Figure 33:
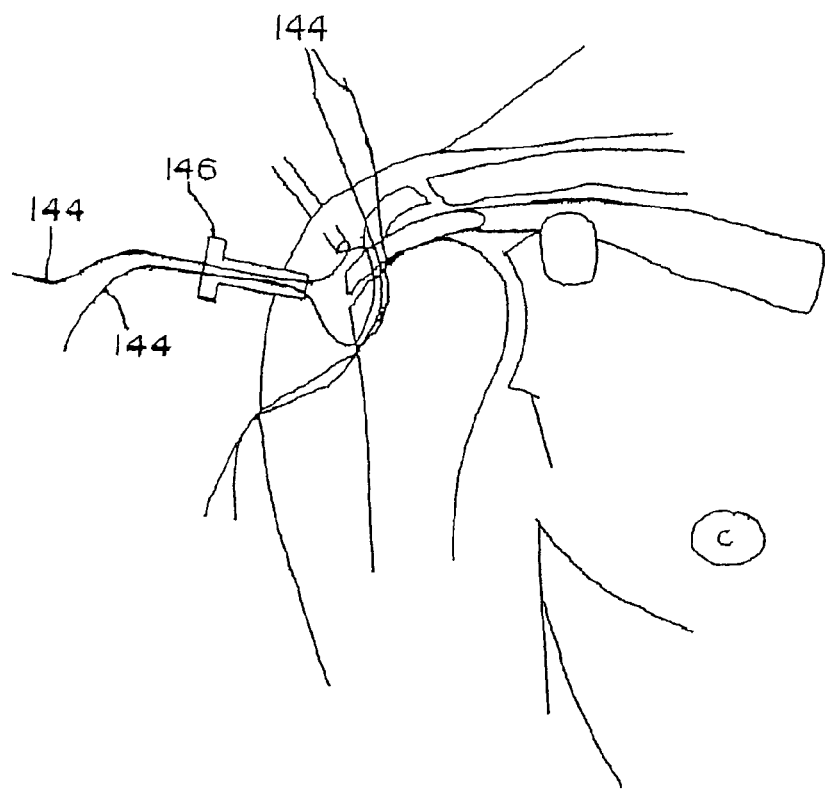
FIG. 33 is a schematic of a way of performing an embodiment of a surgical technique and tying the passed suture of the suture pin device after removing the pin component in accordance with the present invention.

In one embodiment of the rotator cuff repair method, an insertional guide 134 is inserted with a protective inner sheath 137 (FIGS. 28*a-b*). The insertional guide 134 includes a cannulated handle 134A and a cannulated tip 148. The cannulated tip 148 is an elongated rigid tube with a sharp trocar tip 150. The diameter of the rigid tube and trocar tip 150 is slightly larger than that of the leading flexible pin 140 of suture pin device 141 adjacent its sharp leading end 154 (FIG. 29) described below, and is approximately 1.0 to 5.0 mm An inner protective sheath 137 may be used with the insertional guide 134 (FIG. 28*b*). The inner protective sheath 137 screws into the handle 134A of the insertional guide 134. The inner protective sheath 137 has a handle 138 that acts as a stop and prevents the inner protective sheath 137 from extending further into the insertional guide 134 than the level of the protective sheath handle 138. The inner sheath 137 has a blunt end 139 that extends beyond the level of the sharp trocar 150 of the insertional guide 134, providing a non-sharp surface with which to enter the tissue. When the surgeon is prepared to use the sharp trocar tip 150 of insertional guide 134, the inner protective sheath 137 is removed by unscrewing the handle 138 and sliding it out of the insertional guide 134. Optionally, an outer protective sheath may be used that extends over the tip of the insertional guide 134 and provides a blunt end as well. In this embodiment, the outer protective sheath has a longitudinal split so that it may be peeled off of the insertional guide when the surgeon is ready to use the sharp trocar tip 150 of the insertional guide 134. The bore tip 150 is extended into the lateral humeral 20 cortex under direct or arthroscopic visualization (FIG. 30). An arthroscopic retractor 136 may assist the process. Directed by an insertional guide 134 a flexible pin 140 is advanced by a drill through the greater tuberosity of the proximal humerus to exit into an anteromedial supraspinatus rotator cuff footprint. The next step is to reduce the torn edge of the supraspinatus tendon with a soft tissue grasper 138A. The flexible pin 140 is advanced through the cuff (FIG. 31) and out through the superior soft-tissue and skin using a pin director 142 as needed (FIG. 32). The suture-pin devices 141 may pass through the acromion or deltoid as necessary. These steps, namely, advancing the suture pin through the greater tuberosity of the humerus, the supraspinatus rotator cuff tendon and out of the shoulder through the superior soft tissue and skin, are done, as described, in a single unidirectional pass. The drill is switched to a suture pin leading tip and the flexible pin component 140 is removed from the body. The flexible pin 140 is cut from the suture 144. The above steps may be repeated as often as necessary to provide sufficient sutures 144 to secure the torn rotator cuff. For the arthroscopic technique, a tying cannula 146 is then inserted for tensioning and securing suture 144 outside of the humerus inside the shoulder (FIG. 33). The sutures 144 are retrieved and passed in modified Mason-Allen fashion if desired, using free needles (open technique) or an arthroscopic suture passing device. The sutures 144 are tied and the tying steps are repeated. The repair may be reinforced with lateral suture anchors as needed before or after tying the transosseous sutures 144 (FIG. 33).

The suture-pin device 141 comprises two components, a leading flexible pin 140 and a swedged on suture 144. The suture 144 is preferably a durable size #2 suture 144. The pin 140 has a sharp slightly larger diameter trocar tip 154 on its leading end. The remaining pin 140 has a diameter closer to that of the suture 144. The pin 140 is sufficiently long to enter the anterolateral surface of the shoulder, pass through the proximal humerus, rotator cuff, and exit the superior surface of the shoulder with both its leading and trailing ends are exposed. The suture 144 is of similar length.

It is therefore intended that the foregoing detailed description be regarded as illustrative rather than limiting, and that it be understood that it is the following claims, including all equivalents, that are intended to define the spirit and scope of this invention.

I claim:

1. A glenoid implant comprising
a shell having
a protruding surface on a first side arranged to engage the surface of a cavity formed in a glenoid extending between peripheral glenoid surfaces, and
a flat surface on the first side adjacent the protruding surface arranged to engage the peripheral glenoid surfaces adjacent the cavity, and
a wear-resistant articulating surface on a second side opposite the flat surface and the protruding surface.

2. The implant of claim 1 wherein said shell includes a cannulation.

3. The implant of claim 2 which includes a first cannulation arranged to accept a screw compressing the wear-resistant surface into the cavity.

4. The implant of claim 3 which includes cannulations arranged to angularly dispose screws into the glenoid.

5. The implant of claim 4 in which the angularly disposed screws are directed into engagement in a peripheral cortex of the glenoid.

6. The implant of claim 5 in which at least some of the angularly disposed screws are held in locking engagement with the shell and in a fixed depth and direction in the glenoid.

7. The implant of claim 1 wherein said shell includes an ingrowth material to promote bone growth and adhesion of said shell to a glenoid surface.

8. The implant of claim 1 wherein the wear-resistant surface has a thickness dimension.

9. The implant of claim 8 wherein the wear-resistant surface is adapted to extend into the cavity.

10. The implant of claim 1 wherein the wear-resistant surface has a first thickness dimension adjacent one peripheral glenoid surface greater than a second thickness dimension of the wear-resistant surface adjacent a peripheral glenoid surface spaced apart from the first thickness dimension.

11. A glenoid implant comprising
a protruding surface on a first side arranged to engage the surface of a cavity formed in a glenoid extending between peripheral glenoid surfaces, and
a substantially planar wear-resistant articulating surface on a second side opposite the protruding surface.

* * * * *

UNITED STATES PATENT AND TRADEMARK OFFICE
CERTIFICATE OF CORRECTION

PATENT NO. : 9,974,658 B2
APPLICATION NO. : 11/525631
DATED : May 22, 2018
INVENTOR(S) : Chudik Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 2929 days.

Signed and Sealed this
Nineteenth Day of March, 2019

Andrei Iancu
*Director of the United States Patent and Trademark Office*